US006444650B1

(12) United States Patent
Cech et al.

(10) Patent No.: US 6,444,650 B1
(45) Date of Patent: *Sep. 3, 2002

(54) ANTISENSE COMPOSITIONS FOR DETECTING AND INHIBITING TELOMERASE REVERSE TRANSCRIPTASE

(75) Inventors: Thomas R. Cech, Boulder, CO (US); Joachim Lingner, Epalinges (CH); Toru Nakamura, Boulder, CO (US); Karen B. Chapman, Sausalito, CA (US); Gregg B. Morin; Calvin B. Harley, both of Palo Alto, CA (US); William H. Andrews, Richmond, CA (US)

(73) Assignees: Geron Corporation, Menlo Park, CA (US); University Technology Corporation, Boulder, CO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,919

(22) Filed: Mar. 31, 1998

Related U.S. Application Data

(63) Continuation-in-part of application No. 08/974,549, filed on Nov. 19, 1997, now Pat. No. 6,166,178, and a continuation-in-part of application No. 08/974,584, filed on Nov. 19, 1997, which is a continuation-in-part of application No. 08/915,503, filed on Aug. 14, 1997, now abandoned, which is a continuation-in-part of application No. 08/912,951, filed on Aug. 14, 1997, which is a continuation-in-part of application No. 08/911,312, filed on Aug. 14, 1997, now abandoned, which is a continuation-in-part of application No. 08/854,050, filed on May 9, 1997, now Pat. No. 6,261,836, which is a continuation-in-part of application No. 08/851,843, filed on May 6, 1997, now Pat. No. 6,093,809, which is a continuation-in-part of application No. 08/846,017, filed on Apr. 25, 1997, now abandoned, which is a continuation-in-part of application No. 08/844,419, filed on Apr. 18, 1997, now abandoned, which is a continuation-in-part of application No. 08/724,643, filed on Oct. 1, 1996, now abandoned, application No. 09/052,919, which is a continuation-in-part of application No. PCT/US97/17885, filed on Oct. 1, 1997, and a continuation-in-part of application No. PCT/US97/17618, filed on Oct. 1, 1997.

(51) Int. Cl.$^7$ .................. A01N 43/04; A61K 31/70; C02H 21/04
(52) U.S. Cl. .................. 514/44; 536/23.2; 536/23.5
(58) Field of Search .............................. 536/23.2, 23.5; 514/44

(56) References Cited

U.S. PATENT DOCUMENTS 5,583,016 A 12/1996 Villeponteau 5,639,613 A 6/1997 Shay

FOREIGN PATENT DOCUMENTS

WO   WO97/38013   10/1997

OTHER PUBLICATIONS

Gura, Science vol. 270, pp 575–577, 1995.*
EST, Accession No. AA281296, NCBI database, 1997.
EST, Accession No. AA311750, NCBI database, 1997.
EST, Accession No. AA299878, NCBI database, 1997.
Harrington, Lea, et al., (1997) "A Mammalian Telomerase–Associated Protein", *Science* 275:973–977.
Langford, Lauren A., et al. (1997) "Telomerase Activity in Ordinary Meningiomas Predicts Poor Outcome", *Human Pathology* 28(4):416–420.
Nakamura, Toru, M., et al. (1997) "Telomerase Catalytic Subunit Homologs from Fission Yeast and Human", *Science*. 277:955–959.
Harrington, Lea, et al. (1995) "Gel Shift and UV Cross–linking Analysis of *Tetrahymena* Telomerase", *The Journal of Biological Chemistry*, 270(15):8893–8901.
Collins, Kathleen, et al. (1995) "Purification of Tetrahymena Telomerase and Cloning of Genes Encoding of Two Protein Components of the Enzyme", *Cell*, 81:677–686.
Greider, Carol W. (1998) Telomerase and senescence: The history, experiment, the future, *Current Biology*, 8(5):R178–R181.
Kilian, Andrzej, et al. (1997) "Isolation of a candidate human telomerase catalytic subunit gene, which reveals complex splicing patterns in different cell types", *Human Molecular Genetics*, 6(12):2011–2019.
Meyerson, Matthew, et al. (1970) "hEST2, the Putative Human Telomerase Catalytic Subunit Gene, Is Up–Regulated in Tumor Cells and during Immortalization", *Cell* 90:785–795.
Morin, G.B. (1997) "The Implications of Telomerase Biochemistry for Human Disease", *European Journal of Cancer*, 33(5):750–760.

* cited by examiner

*Primary Examiner*—Yvonne Eyler
*Assistant Examiner*—Janet L. Andres
(74) *Attorney, Agent, or Firm*—J. Michael Schiff; David J. Earp; Townsend and Townsend and Crew LLP

(57) ABSTRACT

The present invention provides TRT antisense oligonucleotides, methods of detecting TRT, methods of diagnosing telomerase-related conditions, methods of diagnosing and providing a prognosis for cancer, and methods of treating telomerase-related conditions, including cancer.

14 Claims, 3 Drawing Sheets

FIGURE 1

```
   1 GCAGCGCTGC GTCCTGCTGC GCACGTGGGA AGCCCTGGCC CCGGCCACCC CCGCGATGCC
  61 GCGCGCTCCC CGCTGCCGAG CCGTGCGCTC CCTGCTGCGC AGCCACTACC GCGAGGTGCT
 121 GCCGCTGGCC ACGTTCGTGC GGCGCCTGGG GCCCCAGGGC TGGCGGCTGG TGCAGCGCGG
 181 GGACCCGGCG GCTTTCCGCG CGCTGGTGGC CCAGTGCCTG GTGTGCGTGC CCTGGGACGC
 241 ACGGCCGCCC CCCGCCGCCC CCTCCTTCCG CCAGGTGTCC TGCCTGAAGG AGCTGGTGGC
 301 CCGAGTGCTG CAGAGGCTGT GCGAGCGCGG CGCGAAGAAC GTGCTGGCCT TCGGCTTCGC
 361 GCTGCTGGAC GGGGCCCGCG GGGCCCCCC CGAGGCCTTC ACCACCAGCG TGCGCAGCTA
 421 CCTGCCCAAC ACGGTGACCG ACGCACTGCG GGGGAGCGGG GCGTGGGGGC TGCTGCTGCG
 481 CCGCGTGGGC GACGACGTGC TGGTTCACCT GCTGGCACGC TGCGCGCTCT TTGTGCTGGT
 541 GGCTCCCAGC TGCGCCTACC AGGTGTGCGG GCCGCCGCTG TACCAGCTCG GCGCTGCCAC
 601 TCAGGCCCGC CCCCCGCCAC ACGCTAGTGG ACCCCGAAGG CGTCTGGGAT GCGAACGGGC
 661 CTGGAACCAT AGCGTCAGGG AGGCCGGGGT CCCCCTGGGC CTGCCAGCCC CGGGTGCGAG
 721 GAGGCGCGGG GGCAGTGCCA GCCGAAGTCT CCCGTTGCCC AAGAGGCCCA GGCGTGGCGC
 781 TGCCCCTGAG CCGGAGCGGA CGCCCGTTGG GCAGGGGTCC TGGGCCCACC CGGGCAGGAC
 841 GCGTGGACCG AGTGACCGTG GTTTCTGTGT GGTGTCACCT GCCAGACCCG CCGAAGAAGC
 901 CACCTCTTTG GAGGGTGCGC TCTCTGGCAC GCGCCACTCC CACCCATCCG TGGGCCGCCA
 961 GCACCACGCG GGCCCCCCAT CCACATCGCG GCCACCACGT CCCTGGGACA CGCCTTGTCC
1021 CCCGGTGTAC GCCAGACCA AGCACTTCCT CTACTCCTCA GGCGACAAGG AGCAGCTGCG
1081 GCCCTCCTTC CTACTCAGCT CTCTGAGGCC CAGCCTGACT GGCGCTCGGA GGCTCGTGGA
1141 GACCATCTTT CTGGGTTCCA GGCCCTGGAT GCCAGGGACT CCCCGCAGGT TGCCCCGCCT
1201 GCCCCAGCGC TACTGGCAAA TGCGGCCCCT GTTTCTGGAG CTGCTTGGGA ACCACGCGCA
1261 GTGCCCCTAC GGGGTGCTCC TCAAGACGCA CTGCCCGCTG CGAGCTGCGG TCACCCCAGC
1321 AGCCGGTGTC TGTGCCCGGG AGAAGCCCCA GGGCTCTGTG GCGGCCCCCG AGGAGGAGGA
1381 CACAGACCCC CGTCGCCTGG TGCAGCTGCT CCGCCAGCAC AGCAGCCCCT GGCAGGTGTA
1441 CGGCTTCGTG CGGGCCTGCC TGCGCCGGCT GGTGCCCCCA GGCCTCTGGG GCTCCAGGCA
1501 CAACGAACGC CGCTTCCTCA GGAACACCAA GAAGTTCATC TCCCTGGGGA AGCATGCCAA
1561 GCTCTCGCTG CAGGAGCTGA CGTGGAAGAT GAGCGTGCGG GACTGCGCTT GGCTGCGCAG
1621 GAGCCCAGGG GTTGGCTGTG TTCCGGCCGC AGAGCACCGT CTGCGTGAGG AGATCCTGGC
1681 CAAGTTCCTG CACTGGCTGA TGAGTGTGTA CGTCGTCGAG CTGCTCAGGT CTTTCTTTTA
1741 TGTCACGGAG ACCACGTTTC AAAAGAACAG GCTCTTTTTC TACCGGAAGA GTGTCTGGAG
1801 CAAGTTGAA AGCATTGGAA TCAGACAGCA CTTGAAGAGG GTGCAGCTGC GGGAGCTGTC
1861 GGAAGCAGAG GTCAGGCAGC ATCGGGAAGC CAGGCCCGCC CTGCTGACGT CCAGACTCCG
1921 CTTCATCCCC AAGCCTGACG GGCTGCGGCC GATTGTGAAC ATGGACTACG TCGTGGGAGC
1981 CAGAACGTTC CGCAGAGAAA AGAGGGCCGA GCGTCTCACC TCGAGGGTGA AGGCACTGTT
2041 CAGCGTGCTC AACTACGAGC GGGCGCGGCG CCCCGGCCTC CTGGGCGCCT CTGTGCTGGG
2101 CCTGACGAT ATCCACAGGG CCTGGCGCAC CTTCGTGCTG CGTGTGCGGG CCCAGGACCC
2161 GCCGCCTGAG CTGTACTTTG TCAAGGTGGA TGTGACGGGC GCGTACGACA CCATCCCCCA
2221 GGACAGGCTC ACGGAGGTCA TCGCCAGCAT CATCAAACCC CAGAACACGT ACTGCGTGCG
2281 TCGGTATGCC GTGGTCCAGA AGGCCGCCCA TGGGCACGTC CGCAAGGCCT TCAAGAGCCA
2341 CGTCTCTACC TTGACAGACC TCCAGCCGTA CATGCGACAG TTCGTGGCTC ACCTGCAGGA
2401 GACCAGCCCG CTGAGGGATG CCGTCGTCAT CGAGCAGAGC TCCTCCCTGA ATGAGGCCAG
2461 CAGTGGCCTC TTCGACGTCT TCCTACGCTT CATGTGCCAC CACGCCGTGC GCATCAGGGG
2521 CAAGTCCTAC GTCCAGTGCC AGGGGATCCC GCAGGGCTCC ATCCTCTCCA CGCTGCTCTG
2581 CAGCCTGTGC TACGGCGACA TGGAGAACAA GCTGTTTGCG GGGATTCGGC GGGACGGGCT
2641 GCTCCTGCGT TTGGTGGATG ATTTCTTGTT GGTGACACCT CACCTCACCC ACGCGAAAAC
2701 CTTCCTCAGG ACCCTGGTCC GAGGTGTCCC TGAGTATGGC TGCGTGGTGA ACTTGCGGAA
2761 GACAGTGGTG AACTTCCCTG TAGAAGACGA GGCCCTGGGT GGCACGGCTT TTGTTCAGAT
2821 GCCGGCCCAC GGCCTATTCC CCTGGTGCGG CCTGCTGCTG GATACCCGGA CCCTGGAGGT
2881 GCAGAGCGAC TACTCCAGCT ATGCCCGGAC CTCCATCAGA GCCAGTCTCA CCTTCAACCG
2941 CGGCTTCAAG GCTGGGAGGA ACATGCGTCG CAAACTCTTT GGGGTCTTGC GGCTGAAGTG
3001 TCACAGCCTG TTTCTGGATT TGCAGGTGAA CAGCCTCCAG ACGGTGTGCA CCAACATCTA
3061 CAAGATCCTC CTGCTGCAGG CGTACAGGTT TCACGCATGT GTGCTGCAGC TCCCATTTCA
3121 TCAGCAAGTT TGGAAGAACC CCACATTTTT CCTGCGCGTC ATCTCTGACA CGGCCTCCCT
3181 CTGCTACTCC ATCCTGAAAG CCAAGAACGC AGGGATGTCG CTGGGGGCCA AGGGCGCCGC
3241 CGGCCCTCTG CCCTCCGAGG CCGTGCAGTG GCTGTGCCAC CAAGCATTCC TGCTCAAGCT
3301 GACTCGACAC CGTGTCACCT ACGTGCCACT CCTGGGGTCA CTCAGGACAG CCCAGACGCA
3361 GCTGAGTCGG AAGCTCCCGG GGACGACGCT GACTGCCCTG GAGGCCGCAG CCAACCCGGC
3421 ACTGCCCTCA GACTTCAAGA CCATCTGGA CTGATGGCCA CCCGCCCACA GCCAGGCCGA
3481 GAGCAGACAC CAGCAGCCCT GTCACGCCGG GCTCTACGTC CCAGGGAGGG AGGGGCGGCC
3541 CACACCCAGG CCCGCACCGC TGGGAGTCTG AGGCCTGAGT GAGTGTTTGG CCGAGGCCTG
3601 CATGTCCGGC TGAAGGCTGA GTGTCCGGCT GAGGCCTGAG CGAGTGTCCA GCCAAGGGCT
3661 GAGTGTCCAG CACACCTGCC GTCTTCACTT CCCCACAGGT TGGCGCTCGG CTCCACCCCA
3721 GGGCCAGCTT TTCCTCACCA GGAGCCCGGC TTCCACTCCC CACATAGGAA TAGTCCATCC
3781 CCAGATTCGC CATTGTTCAC CCCTCGCCCT GCCCTCCTTT GCCTTCCACC CCCACCATCC
3841 AGGTGGAGAC CCTGAGAAGG ACCCTGCGGAG CTCTGGGAAT TTGGAGTGAC CAAAGGTGTG
3901 CCCTGTACAC AGGCGAGGAC CCTGCACCTG GATGGGGTC CCTGTGGGTC AAATTGGGGG
3961 GAGGTGCTGT GGGAGTAAAA TACTGAATAT ATGAGTTTTT CAGTTTTGAA AAAAA
```

FIGURE 2

MPRAPRCRAVRSLLRSHYREVLPLATFVRRLGPQGWRLVQRGDPAAFRALVAQCLVCV
PWDARPPPAAPSFRQVSCLKELVARVLQRLCERGAKNVLAFGFALLDGARGGPPEAFT
TSVRSYLPNTVTDALRGSGAWGLLLRRVGDDVLVHLLARCALFVLVAPSCAYQVCGPP
LYQLGAATQARPPPHASGPRRRLGCERAWNHSVREAGVPLGLPAPGARRRGGSASRSL
PLPKRPRRGAAPEPERTPVGQGSWAHPGRTRGPSDRGFCVVSPARPAEEATSLEGALS
GTRHSHPSVGRQHHAGPPSTSRPPRPWDTPCPPVYAETKHFLYSSGDKEQLRPSFLLS
SLRPSLTGARRLVETIFLGSRPWMPGTPRRLPRLPQRYWQMRPLFLELLGNHAQCPYG
VLLKTHCPLRAAVTPAAGVCAREKPQGSVAAPEEEDTDPRRLVQLLRQHSSPWQVYGF
VRACLRRLVPPGLWGSRHNERRFLRNTKKFISLGKHAKLSLQELTWKMSVRDCAWLRR
SPGVGCVPAAEHRLREEILAKFLHWLMSVYVVELLRSFFYVTETTFQKNRLFFYRKSV
WSKLQSIGIRQHLKRVQLRELSEAEVRQHREARPALLTSRLRFIPKPDGLRPIVNMDY
VVGARTFRREKRAERLTSRVKALFSVLNYERARRPGLLGASVLGLDDIHRAWRTFVLR
VRAQDPPPELYFVKVDVTGAYDTIPQDRLTEVIASIIKPQNTYCVRRYAVVQKAAHGH
VRKAFKSHVSTLTDLQPYMRQFVAHLQETSPLRDAVVIEQSSSLNEASSGLFDVFLRF
MCHHAVRIRGKSYVQCQGIPQGSILSTLLCSLCYGDMENKLFAGIRRDGLLLRLVDDF
LLVTPHLTHAKTFLRTLVRGVPEYGCVVNLRKTVVNFPVEDEALGGTAFVQMPAHGLF
PWCGLLLDTRTLEVQSDYSSYARTSIRASLTFNRGFKAGRNMRRKLFGVLRLKCHSLF
LDLQVNSLQTVCTNIYKILLLQAYRFHACVLQLPFHQQVWKNPTFFLRVISDTASLCY
SILKAKNAGMSLGAKGAAGPLPSEAVQWLCHQAFLLKLTRHRVTYVPLLGSLRTAQTQ
LSRKLPGTTLTALEAAANPALPSDFKTILD

ANTISENSE COMPOSITIONS FOR DETECTING AND INHIBITING TELOMERASE REVERSE TRANSCRIPTASE

CROSS REFERENCE TO RELATED APPLICATION

The present application is a continuation-in-part of U.S. patent application Ser. No. 08/974,549, filed Nov. 19, 1997 now U.S. Pat. No. 6,166,178; and a continuation-in-part of U.S. patent application Ser. No. 08/974,584, filed Nov. 19, 1997, both of which are continuation-in-part applications of U.S. patent application Ser. No. 08/915,503 filed Aug. 14, 1997, now abandoned, U.S. patent application Ser. No. 08/912,951 filed Aug. 14, 1997, and U.S patent application Ser. No. 08/911,312, all filed Aug. 14, 1997 now abandoned, all three of which are continuation-in-part applications of U.S., patent application Ser. No. 08/854,050, filed May 9, 1997 now U.S. Pat. No. 6,261,836, which is a continuation-in-part application of U.S. patent application Ser. No. 08/851,843, filed May 6, 1997 now U.S. Pat. No. 6,093,809, which is a continuation-in-part application of U.S. patent application Ser. No. 08/846,017, filed Apr. 25, 1997 now abandoned, which is a continuation-in-part application of U.S. patent application Ser. No. 08/844,419, filed Apr. 18, 1997 now abandoned, which is a continuation-in-part application, U.S. patent application Ser. No. 08/724,643, filed Oct. 1, 1996 now abandoned. This application is also a continuation-in-part of Patent Convention Treaty Patent Application Serial No.: PCT/US97/17885 and to Patent Convention Treaty Patent Application Serial No.: PCT/US97/17618, both filed on Oct. 1, 1997. Each of the aforementioned applications is explicitly incorporated herein by reference in its entirety and for all purposes.

FIELD OF THE INVENTION

The present invention provides TRT antisense oligonucleotides, methods of detecting TRT, methods of diagnosing telomerase-related conditions, methods of diagnosing and providing a prognosis for cancer, and methods of treating telomerase-related conditions, including cancer, with TRT antisense oligonucleotides.

BACKGROUND OF THE INVENTION

The following discussion is intended to introduce the field of the present invention to the reader. The citation of various references in this section should not be construed as an admission of prior invention.

It has long been recognized that complete replication of the ends of eukaryotic chromosomes requires specialized cell components (Watson, 1972, *Nature New Biol.*, 239:197; Olovnikov, 1973, *J. Theor. Biol.*, 41:181). Replication of a linear DNA strand by conventional DNA polymerases requires an RNA primer, and can proceed only 5' to 3'. When the RNA bound at the extreme 5' ends of eukaryotic chromosomal DNA strands is removed, a gap is introduced, leading to a progressive shortening of daughter strands with each round of replication. This shortening of telomeres, the protein-DNA structures physically located on the ends of chromosomes, is thought to account for the phenomenon of cellular senescence or aging of normal human somatic cells in vitro and in vivo. The length and integrity of telomeres is thus related to entry of a cell into a senescent stage (i.e., loss of proliferative capacity), or the ability of a cell to escape senescence, i.e., to become immortal. The maintenance of telomeres is a function of a telomere-specific DNA polymerase known as telomerase. Telomerase is a ribonucleoprotein (RNP) that uses a portion of its RNA moiety as a template for telomeric DNA synthesis (Morin, 1997, *Eur. J. Cancer* 33:750).

Consistent with the relationship of telomeres and telomerase to the proliferative capacity of a cell (i.e., the ability of the cell to divide indefinitely), telomerase activity is detected in immortal cell lines and an extraordinarily diverse set of tumor tissues, but is not detected (i.e., was absent or below the assay threshold) in normal somatic cell cultures or normal tissues adjacent to a tumor (see, U.S. Pat. Nos. 5,629,154; 5,489,508; 5,648,215; and 5,639,613; see also, Morin, 1989, *Cell* 59: 521; Shay and Bacchetti 1997, *Eur. J. Cancer* 33:787; Kim et al., 1994, *Science* 266:2011; Counter et al., 1992, *EMBO J.* 11:1921; Counter et al., 1994, *Proc. Natl. Acad. Sci. U.S.A.* 91, 2900; Counter et al., 1994, *J. Virol.* 68:3410). Moreover, a correlation between the level of telomerase activity in a tumor and the likely clinical outcome of the patient has been reported (e.g., U.S. Pat. No. 5,639,613, supra; Langford et al., 1997, *Hum. Pathol.* 28:416). Human telomerase is thus an ideal target for diagnosing and treating human diseases relating to cellular proliferation and senescence, such as cancer.

SUMMARY OF THE INVENTION

The present invention provides TRT antisense polynucleotides, which are useful for detecting, diagnosing, and treating telomerase-related conditions.

In one aspect, the present invention provides an isolated, synthetic, substantially pure, or recombinant polynucleotide having a sequence that is at least about ten nucleotides in length to at least about 100 nucleotides in length. This polynucleotide comprises a sequence that is substantially complementary or substantially identical to a contiguous sequence of an hTRT nucleic acid that has the nucleotide sequence of FIG. 1.

In one aspect, the present invention provides an isolated, synthetic, substantially pure, or recombinant polynucleotide having a sequence that is at least about ten nucleotides in length to at least about 100 nucleotides in length. This polynucleotide comprises a sequence exactly complementary or identical to a contiguous sequence of a nucleic acid encoding the hTRT protein of FIG. 2.

In one embodiment, the hTRT polynucleotide comprises a sequence that is exactly complementary or identical to a contiguous sequence of an hTRT nucleic acid having the nucleotide sequence of FIG. 1.

In one embodiment, the polynucleotide is a DNA or an RNA. In one embodiment, the polynucleotide comprises one or more non-naturally occurring, synthetic nucleotides.

In one embodiment, the polynucleotide is identical to said contiguous sequence of a nucleic acid encoding the hTRT protein of FIG. 1. In one embodiment, the polynucleotide is exactly complementary to said contiguous sequence of a nucleic acid encoding the hTRT protein of FIG. 1.

In one embodiment, the polynucleotide is an antisense polynucleotide. In one embodiment, the polynucleotide is at least about 20 nucleotides in length to at least about 50 nucleotides in length.

In one embodiment, the polynucleotide inhibits telomerase activity by at least about 50% in transformed cells ex vivo, as compared to control cells that are not treated with the polynucleotide. In one embodiment, the polynucleotide inhibits telomerase expression by at least about 50% in vitro, as compared to control expression reactions that lack the polynucleotide. In one embodiment, the polynucleotide is selected from the group consisting of PS-ODN number 3, 4, 7, 8, 16, 21, 25, 26, 27, 28, 29, 33, 40, 41, 43, 44, 45, 46, 47, 48, 49, 50, 51, 52, 53, 54, 62, 68, 69, 70, 71, 72, 73, 74, 75, 76, 77, 80, 81, 82, 83, 84, 85, 86, 87, 88, 93, 94, 96, 100, 112, 114, 130, 143, 144, 151, 152, 201, 202, 203, 208, 209, 210, 211, 212, 213, 230, 237, and 241.

BRIEF DESCRIPTION OF THE DRAWINGS

FIG. 1 presents the nucleotide sequence of a cDNA (SEQ ID NO:1) encoding a naturally occurring human telomerase reverse transcriptase (hTRT) protein.

FIG. 2 presents the amino acid sequence (SEQ ID NO:2) of a naturally occurring, 1132-residue human telomerase reverse transcriptase (hTRT) protein.

DETAILED DESCRIPTION

I. Introduction

Figure 3:
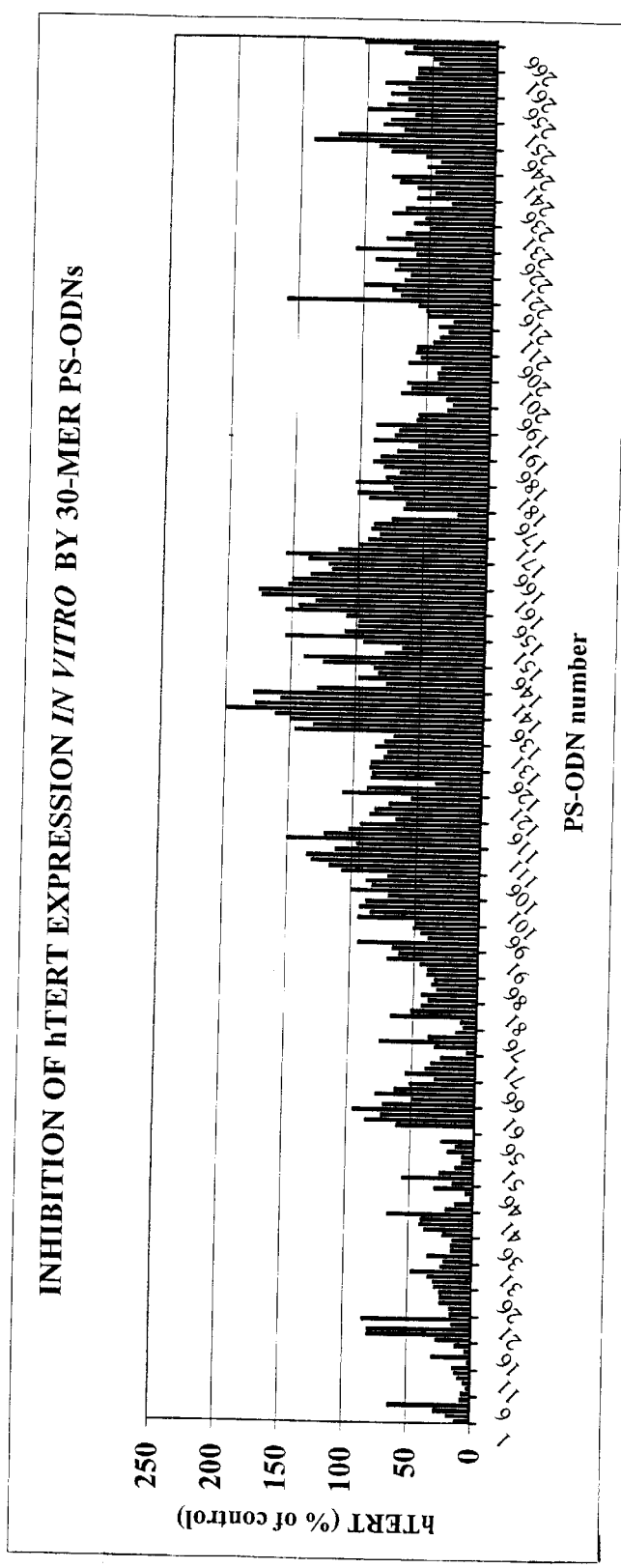
FIG. 3 shows inhibition of hTRT expression in vitro by hTRT sequence-specific antisense phosphorothioate oligonucleotides (PS-ODN). Each bar in the graph represents the in vitro inhibitory activity of a specific oligonucleotide, numbered starting with P,S-ODN #1. The PS-ODN are a series of 30-mers that span the hTRT mRNA and are offset one from the next by fifteen nucleotides. For example, ODN #1 corresponds to positions 16–35 of hTRT and is TCCCACGTGCGCAGCAGGACGCAGCGCTGC. ODN #2 corresponds to positions 31–60 and is GGCATCGCGGGGGTGGCCGGGGCCAGGGCT (SEQ ID NO:4), and so one to the end of the RNA (see the cDNA sequence of FIG. 1, which represents an hTRT RNA sequence). The data are presented as a normalized percentage of the control with no added PS-ODN.

Telomerase is a ribonucleoprotein complex (RNP) comprising an RNA component and a catalytic protein component. The catalytic protein component of human telomerase, hereinafter referred to as telomerase reverse transcriptase ("hTRT"), has been cloned, and protein, cDNA, and genomic sequences determined. See, e.g., Nakamura et al., 1997, Science 277:955, and copending U.S. patent applications Ser. Nos. 08/912,951 and 08/974,549. The sequence of a full-length native hTRT has been deposited in GenBank (Accession No. AF015950), and plasmid and phage vectors having hTRT coding sequences have been deposited with the American Type Culture Collection, Rockville, Md. (accession numbers 209024, 209016, and 98505). The catalytic subunit protein of human telomerase has also been referred to as "hEST2" (Meyerson et al., 1997, Cell 90:785), "hTCS1" (Kilian et al., 1997, Hum. Mol. Genet. 6:2011), "TP2" (Harrivigton et al., 1997, Genes Dev. 11:3109), and "hTERT" (e.g., Greider, 1998, Curr. Biol. 8:R178–R181). The RNA component of human telomerase (hTR) has also been characterized (see U.S. Pat. No. 5,583,016).

Human TRT is of extraordinary interest and value because, inter alia, telomerase activity in human cells and other mammalian cells correlates with cell proliferative capacity, cell immortality, and the development of a neoplastic phenotype. hTRT antisense polynucleotides, including the exemplary polynucleotides described herein, hybridize to and/or amplify naturally occurring hTRT genes or RNA. Such oligonucleotides are thus useful for diagnostic or prognostic applications to telomerase related conditions, including cancer. The hTRT antisense polynucleotides of the invention are also useful as therapeutic agents, e.g., antisense oligonucleotides, ribozymes, or triplex compositions, for inhibition of telomerase expression and activity (e.g., telomerase catalytic activity, infra).

The invention thus provides antisense oligonucleotide reagents, which can be used to detect expression of hTRT or reduce expression and activity of hTRT gene products in vitro, ex vivo, or in vivo. Administration of the antisense reagents of the invention to a target cell results in reduced telomerase activity, and is particularly useful for treatment of diseases characterized by high telomerase activity (e.g., cancers). Detection and inhibition of hTRT expression can be performed in a cell or cell extracts from a human, a mammal, a vertebrate, or other eukaryote.

The antisense polynucleotides of the invention are characterized by their ability to specifically hybridize to naturally occurring and synthetic hTRT nucleic acids, e.g., the hTRT gene, including any upstream, flanking, noncoding, and transcriptional control elements, hTRT pre-mRNA, mRNA, cDNA and the like. The hTRT antisense polynucleotides of the invention are typically at least 7–10 nucleotides in length to typically more 20 nucleotides up to about 100 nucleotides in length, preferably approximately 30 nucleotides in length. Such antisense oligonucleotides are used to detect the presence of hTRT nucleic acid in a biological sample, for diagnosis and/or prognosis of telomerase related conditions, e.g., cancers of any of a wide variety of types, including solid tumors and leukemias, diseases of cell proliferation, disease resulting from cell senescence (particularly diseases of aging), immunological disorders, infertility, disease of immune dysfunction, etc.

The antisense polynucleotides of the invention also can be used to inhibit telomerase expression in vitro, to inhibit telomerase expression and activity in cells ex vivo, and can be used in vivo as therapeutic agents for the treatment of telomerase-related conditions listed above, including cancers of a wide variety of types (see, e.g., exemplary cancers listed in U.S. patent application Ser. No. 08/974,549; and U.S. patent application Ser. No. 08/974,584). In one embodiment of the invention, the antisense polynucleotides are 30 nucleotides in length, and have the ability to inhibit telomerase expression at least by 50% in vitro (see, e.g., the antisense oligonucleotides of FIG. 3). In another embodiment of the invention, the antisense polynucleotides are 30 nucleotides in length, and have the ability to inhibit telomerase expression and activity at least 50% in transformed cells ex vivo (see, e.g., exemplary antisense hTRT oligonucleotides listed in Table 1).

II. Definitions

As used herein, the following terms have the meanings ascribed to them unless specified otherwise.

As used herein, the terms "nucleic acid" and "polynucleotide" are used interchangeably. Use of the term "polynucleotide" includes oligonucleotides (i.e., short polynucleotides). This term also refers to deoxyribonucleotides, ribonucleotides, and naturally occurring variants, and can also refer to synthetic and/or non-naturally occurring nucleic acids (i.e., comprising nucleic acid analogues or modified backbone residues or linkages), such as, for example and without limitation, phosphorothioates, phosphoramidates, methyl phosphonates, chiral-methyl phosphonates, 2-O-methyl ribonucleotides, peptide-nucleic acids (PNAs), and the like, as described herein.

As used herein "oligonucleotides" or "oligomers" refer to a nucleic acid sequence of approximately 7 nucleotides or greater in length, and up to as many as approximately 100 nucleotides in length, which can be used as a primer, probe or amplimer. Oligonucleotides are often between about 10 and about 50 nucleotides in length, more often between about 14 and about 35 nucleotides, very often between about 15 and about 30 nucleotides, and the terms oligonucleotides or oligomers can also refer to synthetic and/or non-naturally occurring nucleic acids (i.e., comprising nucleic acid analogies or modified backbone residues or linkages).

A polynucleotide "specifically hybridizes" or "specifically binds" to a target polynucleotide if the polynucleotide hybridizes to the target under stringent conditions. As used herein, "stringent hybridization conditions" or "stringency" refers to conditions in a range from about 5° C. to about 20° C. or 25° C. below the melting temperature ($T_m$) of the target sequence and a probe with exactly or nearly exactly complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) *Methods in Enzymology,* Vol. 152: *Guide to Molecular Cloning Techniques,* San Diego: Academic Press, Inc.; Sambrook et al. (1989) *Molecular Cloning,: A Laboratory Manual,* 2nd Ed., Vols. 1–3, Cold Spring Harbor Laboratory hereinafter, "Sambrook"); and *Current Protocols in Molecular Biology* (Ausubel et al., eds. through and including the 1997 supplement), incorporated herein by reference). As indicated by standard references, a simple estimate of the $T_m$ value may be calculated by the equation: $T_m=81.5+0.41(\% G+C)$, when a nucleic acid is in aqueous solution at 1 M NaCl (see e.g., Anderson and Young, *Quantitative Filter Hybridization in Nucleic Acid Hybridization* (1985)). Other references include more sophisticated computations, which take structural as well as sequence characteristics into account for the calculation of $T_m$. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, e.g., Sambrook, supra and Ausubel et al. supra. Typically, stringent hybridization conditions are salt concentrations less than about 1.0 M sodium ion, typically about 0.01 to 1.0 M sodium ion at pH 7.0 to 8.3, and temperatures at least about 30° C. for short nucleic acids (e.g., 7 to 50 nucleotides) and at least about 60° C. for long nucleic acids (e.g., greater than 50 nucleotides). As noted, stringent conditions may also be achieved with the addition of destabilizing agents such as formamide, in which case lower temperatures may be employed.

An "identical" polynucleotide refers to a polynucleotide that has the same sequence as the reference nucleotide subsequence to which the polynucleotide is being compared. An "exactly complementary" polynucleotide refers to a polynucleotide whose complement has the same sequence as the reference nucleotide subsequence to which the polynucleotide is being compared.

A "substantially complementary" polynucleotide and a "substantially identical" polynucleotide have the ability to specifically hybridize to a reference gene, DNA, cDNA, or mRNA, e.g., the hTRT nucleotide sequence of FIG. 1 and its exact complement.

An "antisense" polynucleotide is a polynucleotide that is substantially complementary to a target polynucleotide and has the ability to specifically hybridize to the target polynucleotide.

A "telomerase-related condition" refers to a diseases and disease conditions in a patient and/or a cell, characterized by under- or over-expression of telomerase or hTRT gene products. In addition to cancer, which is characterized by over-expression of telomerase, such conditions include diseases of cell proliferation, e.g., hyperplasias, disease resulting from cell senescence (particularly diseases of aging), immunological disorders, infertility, etc.

As used herein, "isolated," when referring to a molecule or composition, such as, for example, an oligonucleotide, means that the molecule or composition is separated from at least one other compound, such as other oligonucleotides or other contaminants with which it is associated in vivo or in its naturally occurring state or synthetic state. An isolated composition can also be substantially pure.

A "synthetic" oligonucleotide refers to a polynucleotide synthesized using in vitro chemical methods, e.g., by using a machine that synthesizes polynucleotides using the phosphodiester method, the diethylphosphoramidite method, the phosphotriester methods, the solid support method, and other methods known to those skilled in the art.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

As used herein, the term "substantially pure," or "substantially purified," when referring to a composition comprising a specified reagent, such as an oligonucleotide, means that the specified reagent is at least about 75%, or at least about 90%, or at least about 95%, or at least about 99% or more of the composition (not including, e.g., solvent or buffer). Thus, for example, an antisense oligonucleotide preparation that specifically binds an hTRT gene or mRNA is substantially purified.

"TRT" activity refers to one or more of the activities found in naturally-occurring full-length TRT proteins. These activities include "telomerase catalytic activity" (the ability to extend a DNA primer that functions as a telomerase substrate by adding a partial, one, or more than one repeat of a sequence, e.g., TTAGGG, encoded by a template nucleic acid, e.g., hTR), "telomerase conventional reverse: transcriptase activity" (see Morin, 1997, supra, and Spence et al., 1995, *Science* 267:988); "nucleolytic activity" (see Morin, 1997, supra; Collins and Grieder, 1993, *Genes and Development* 7:1364; Joyce and Steitz, 1987, *Trends Biochem. Sci.* 12:288); "primer (telomere) binding activity" (see, Morin, 1997, supra; Collins et al., 1995, *Cell* 81:677; Harrington et al., 1995, *J. Biol. Chem.* 270:8893); "dNTP binding activity" (Morin, 1997, supra; Spence et al., supra); and "RNA (e.g., hTR) binding activity" (see Morin, 1997, supra; Harrington et al., 1997, *Science* 275:973; Collins et al., 1995, *Cell* 81:677,).

"TRT" refers to telomerase reverse transcriptase protein, and "hTRT" refers to human telomerase reverse transcriptase protein.

The term "hTRT" is intended to refer to alleles, conservatively modified variants, polymorphic variants, and interspecies homologues of hTRT encoded by nucleic acids that specifically hybridize to the hTRT nucleic acid sequence provided in FIG. 1.

"Conservatively modified variants" applies to both amino acid and nucleic acid sequences. With respect to particular nucleic acid sequences, conservatively modified variants refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton (1984) *Proteins,* W. H. Freeman and Company.

III. How to Make Antisense Polynucleotides

As described herein, the present invention provides antisense polynucleotides, which have the ability to specifically hybridize to hTRT. Without intending to be limited to any particular mechanism, it is believed that antisense oligonucleotides bind to, and interfere with the translation of, the sense hTRT mRNA. Alternatively, the antisense molecule may render the hTRT mRNA susceptible to nuclease digestion, interfere with transcription, interfere with processing, localization or otherwise with RNA precursors ("pre-mRNA"), repress transcription of mRNA from the hTRT gene, or act through some other mechanism. However, the particular mechanism by which the antisense molecule reduces hTRT expression is not critical.

Generally, to assure specific hybridization, the antisense sequence is substantially complementary to the target hTRT mRNA sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to hTRT RNA or its gene is retained as a functional property of the polynucleotide.

In one embodiment, the antisense sequence is complementary to relatively accessible sequences of the hTRT mRNA (e.g., relatively devoid of secondary structure). These sequences can be determined by analyzing predicted RNA secondary structures using, for example, the MFOLD program (Genetics Computer Group, Madison Wis.) and testing in vitro or in vivo as is known in the art. FIG. 3 and TAble 1 show examples of oligonucleotides that are useful in cells for antisense suppression of hTRT function and are capable of hybridizing to hTRT (i.e., are substantially complementary to hTRT). Another useful method for identifying effective antisense compositions uses combinatorial arrays of oligonucleotides (see, e.g., Milner et al., 1997, *Nature Biotechnology* 15:537).

A. Triplex-forming Antisense Polynucleotides

As one embodiment of the antisense molecules described herein, the present invention provides polynucleotides that bind to double-stranded or duplex hTRT nucleic acids (e.g., in a folded region of the hTRT RNA or in the hTRT gene), forming a triple helix-containing, or "triplex" nucleic acid. Triple helix formation results in inhibition of hTRT expression by, for example, preventing transcription of the hTRT gene, thus reducing or eliminating telomerase activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides of the invention are constructed using the base-pairing rules of triple helix formation (see, e.g., Cheng et al., 1988, *J. Biol. Chem.* 263: 15110; Ferrin and Camerini-Otero, 1991, *Science* 354:1494; Ramdas et al., 1989, *j. Biol. Chem.* 264:17395; Strobel et al., 1991, *Science* 254:1639; and Rigas et al., 1986, *Proc. Natl. Acad. Sci. U.S.A.* 83: 9591; each of which is incorporated herein by reference) and the hTRT MnRNA and/or gene sequence. Typically, the triplex-forming oligonucleotides of the invention comprise a specific sequence of from about 10 to at least about 25 nucleotides or longer "complementary" to a specific sequence in the hTRT RNA or gene (i.e., large enough to form a stable triple helix, but small enough, depending on the mode of delivery, to administer in vivo, if desired). In this context, "complementary" means able to form a stable triple helix. In one embodiment, oligonucleotides are designed to bind specifically to the regulatory regions of the hTRT gene (e.g., the hTRT 5'-flanking sequence, promoters, and enhancers) or to the transcription initiation site, (e.g., between −10 and +10 from the transcription initiation site). For a review of recent therapeutic advances using triplex DNA, see Gee et al., in Huber and Carr, 1994, *Molecular and Immunologic Approaches,* Futura Publishing Co, Mt Kisco N.Y. and Rininsland et al., 1997, *Proc. Natl. Acad. Sci. USA* 94:5854, which are both incorporated herein by reference.

B. Ribozymes

In another embodiment, the present invention provides ribozymes useful for inhibition of hTRT telomerase activity. The ribozymes of the invention bind and enzymatically cleave and inactivate hTRT mRNA. Useful ribozymes can comprise 5'- and 3'-terminal sequences complementary to the hTRT mRNA and can be engineered by one of skill on the basis of the hTRT mRNA sequence disclosed herein (see PCT publication WO 93/23572, supra). Ribozymes of the invention include those having characteristics of group I intron ribozymes (Cech, 1995, *Biotechnology* 13:323) and others of hammerhead ribozymes (Edgington, 1992, *Biotechnology* 10:256).

Ribozymes of the invention include those having cleavage sites such as GUA, GUU and GUC. Other optimum cleavage sites for ribozyme-mediated inhibition of telomerase activity in accordance with the present invention include those described in PCT publications WO 94/02595 and WO 93/23569, both incorporated herein by reference. Short RNA oligonucleotides between 15 and 20 ribonucleotides in length corresponding to the region of the target hTRT gene containing the cleavage site can be evaluated for secondary structural features that may render the oligonucleotide more desirable. The suitability of cleavage sites may also be evaluated by testing accessibility to hybridization with complementary oligonucleotides using ribonuclease protection assay, or by testing for in vitro ribozyme activity in accordance with standard procedures known in the art.

As described by Hu et al., PCT publication WO 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

C. Synthesis of Antisense Polynucleotides

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA that hybridizes to hTRT mRNA can be made by inserting (ligating) an hTRT DNA sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

The present invention also provides hTRT antisense polynucleotides (RNA, DNA. or modified) that can be produced by direct chemical synthesis. Chemical synthesis is generally preferred for the production of oligonucleotides or for oligonucleotides and polynucleotides containing nonstandard nucleotides (e.g., probes, primers and antisense oligonucleotides). Direct chemical synthesis of nucleic acids can be accomplished by methods known in the art, such as the phosphotriester method of Narang et al., 1979, *Meth. Enzymol.* 68:90; the phosphodiester method of Brown et al., *Meth. Enzymol.* 68:109 (1979); the diethylphosphoramidite method of Beaucage et al., *Tetra. Lett.,* 22:1859 (1981); and the solid support method of U.S. Pat. No. 4,458,066.

Chemical synthesis typically produces a single stranded oligonucleotide, which may be converted into double stranded DNA by hybridization with a complementary sequence, or by polymerization with a DNA polymerase and an oligonucleotide primer using the single strand as a template. One of skill will recognize that while chemical synthesis of DNA is often limited to sequences of about 100 or 150 bases, longer sequences may be obtained by the ligation of shorter sequences or by more elaborate synthetic methods.

It will be appreciated that the hTRT polynucleotides and oligonucleotides of the invention can be made using nonstandard bases (e.g., other than adenine, cytidine, guanine, thymine, and uridine) or nonstandard backbone structures to provides desirable properties (e.g., increased nuclease-resistance, tighter-binding, stability or a desired $T_M$). Techniques for rendering oligonucleotides nuclease-resistant include those described in PCT publication WO 94/12633. A wide variety of useful modified oligonucleotides may be produced, including oligonucleotides having a peptide-nucleic acid (PNA) backbone (Nielsen et al., 1991, *Science* 254:1497) or incorporating 2'-O-methyl ribonucleotides, phosphorothioate nucleotides, methyl phosphonate nucleotides, phosphotriester nucleotides, phosphorothioate nucleotides, phosphoramidates. Still other useful oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$, where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a folate group; a reporter group; an intercalator; a group for improving the pharmacokinetic properties of an oligonucleotide; or a group for improving the pharmacodynamic properties of an oligonucleotide and other substituents having similar properties. Folate, cholesterol or other groups that facilitate oligonucleotide uptake, such as lipid analogs, may be conjugated directly or via a linker at the 2' position of any nucleoside or at the 3' or 5' position of the 3'-terminal or 5'-terminal nucleoside, respectively. One or more such conjugates may be used. Oligonucleotides may also have sugar mimetics such as cyclobutyls in place of the pentofuranosyl group. Other embodiments may include at least one modified base form or "universal base" such as inosine, or inclusion of other nonstandard bases such as queosine and wybutosine as well as acetyl-, methyl-, thio- and similarly modified forms of adenine, cytidine, guanine, thymine, and uridine which are not as easily recognized by endogenous endonucleases.

The invention further provides oligonucleotides having backbone analogues such is phosphodiester, phosphorothioate, phosphorothioate, methylphosphonate, phosphoramidate, alkyl phosphotriester, sulfamate, 3'-thioacetal, methylene(methylimino), 3'-N-carbamate, morpholino carbamate, chiral-methyl phosphonates, nucleotides with short chain alkyl or cycloalkyl intersugar linkages, short chain heteroatomic or heterocyclic intersugar ("backbone") linkages, or $CH_2$—NH—O—$CH_2$, $CH_2$—N($CH_3$)—$OCH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$), or mixtures of the same. Also useful are oligonucleotides having morpholino backbone structures (U.S. Pat. No. 5,034,506).

Useful references include *Oligonucleotides and Analogues, A Practical Approach,* edited by F. Eckstein, IRL Press at Oxford University Press (1991); *Antisense Strategies, Annals of the New York Academy of Sciences,* Volume 600, Eds. Baserga and Denhardt (NYAS 1992); Milligan et al., Jul. 9, 1993, *J. Med. Chem.* 36(14):1923–1937; *Antisense Research and Applications* (1993, CRC Press), in its entirety and specifically Chapter 15, by Sanghvi, entitled "Heterocyclic base modifications in nucleic acids and their applications in antisense oligonucleotides;" and *Antisense Therapeutics,* ed. Sudhir Agrawal (Humana Press, Totowa, N.J., 1996).

D. Labeled Antisense Oligonucleotides

It is often useful to label the antisense polynucleotides of the invention, for example, when the hTRT polynucleotides are to be used for detection of hTRT expression, and for diagnosis and prognosis of telomerase related conditions. The labels may be incorporated by any of a number of means well known to those of skill in the art. Suitable labels are any composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, digoxigenin, haptens and proteins for which antisera or monoclonal antibodies are available, or nucleic acid molecules with a sequence complementary to a target. The label often generates a measurable signal, such as radioactivity, that can be used to quantitate the amount of bound detectable moiety.

The label can be incorporated in or attached to a polynucleotide either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules.

IV. Exemplary Antisense Polynucleotides

A series of 30-mer antisense oligonucleotides, which span the entire hTRT sequence, are exemplary embodiments of the present invention (see FIG. 3). These oligonucleotides were systematically assayed for the ability to inhibit hTRT expression in vitro. The results of the experiment are presented in FIG. 3 (see also Example I). Any suitable series of hTRT antisense oligonucleotides can be tested in a similar fashion. For example, a series of 20-mer antisense oligonucleotides, offset one from the next by 10 nucleotides can be synthesized and tested in the same manner. A series of 25-mer, 35-mer, or 15-mer oligonucleotides can be examined in the same manner.

Selected oligonucleotides from the series of FIG. 3 were then tested ex vivo for their ability to inhibit hTRT expression in tumor cells (see Example II). The hTRT antisense oligonucleotides active for inhibiting telomerase activity ex vivo in tumor cells were than assayed for their long term cell culture effects on hTRT expression, telomerase activity, telomere dynamics, and cell proliferation (see Example II). The oligonucleotides of Table I represent exemplary oligonucleotides that inhibited telomerase activity ex vivo.

TABLE I

| | | hTRT AS 30-mers: |
|---|---|---|
| PS-ODN# | Position *(3'–5') | 5'-AS sequence-3' SEQ ID NO; |
| 3 | 31–60 | SEQ ID NO: 4 GGCATCGCGGGGGTGGCCGGGGCCAGGGCT |
| 4 | 46–75 | SEQ ID NO: 5 CAGCGGGGAGCGCGCGGCATCGCGGGGGTG |
| 7 | 91–120 | SEQ ID NO: 6 AGCACCTCGCGGTAGTGGCTGCGCAGCAGG |
| 8 | 106–135 | SEQ ID NO: 7 AACGTGGCCAGCGGCAGCACCTCGCGGTAG |
| 16 | 226–255 | SEQ ID NO: 8 GCGGGGGGCGGCCGTGCGTCCCAGGGCACG |
| 21 | 301–330 | SEQ ID NO: 9 CCGCGCTCGCACAGCCTCTGCAGCACTCGG |
| 25 | 361–390 | SEQ ID NO: 10 GGGGGGCCCCCGCGGGCCCCGTCCAGCAGC |
| 26 | 376–405 | SEQ ID NO: 11 GTGGTGAAGGCCTCGGGGGGGCCCCCGCGG |
| 27 | 391–420 | SEQ ID NO: 12 TAGCTGCGCACGCTGGTGGTGAAGGCCTCG |
| 28 | 406–435 | SEQ ID NO: 13 ACCGTGTTGGGCAGGTAGCTGCGCACGCTG |
| 29 | 421–450 | SEQ ID NO: 14 CGCAGTGCGTCGGTCACCGTGTTGGGCAGG |
| 33 | 481–510 | SEQ ID NO: 15 AGGTGAACCAGCACGTCGTCGCCCACGCGG |
| 40 | 586–615 | SEQ ID NO: 16 GGGGGCCGGGCCTGAGTGGCAGCGCCGAGC |
| 41 | 601–630 | SEQ ID NO: 17 CCACTAGCGTGTGGCGGGGGCCGGGCCTGA |
| 43 | 631–660 | SEQ ID NO: 18 GCCCGTTCGCATCCCAGACGCCTTCGGGGT |
| 44 | 646–675 | SEQ ID NO: 19 ACGCTATGGTTCCAGGCCCGTTCGCATCCC |
| 45 | 661–690 | SEQ ID NO: 20 ACCCCGGCCTCCCTGACGCTATGGTTCCAG |
| 46 | 676–705 | SEQ ID NO: 21 GGCAGGCCCAGGGGGACCCCGGCCTCCCTG |
| 47 | 691–720 | SEQ ID NO: 22 CTCGCACCCGGGGCTGGCAGGCCCAGGGGG |
| 48 | 706–735 | SEQ ID NO: 23 CTGCCCCCGCGCCTCCTCGCACCCGGGGCT |
| 49 | 721–750 | SEQ ID NO: 24 AGACTTCGGCTGGCACTAGCCCCCGCGCCTC |
| 50 | 736–765 | SEQ ID NO: 25 CTCTTGGGCAACGGCAGACTTCGGCTGGCA |
| 51 | 751–780 | SEQ ID NO: 26 GCGCCACGCCTGGGCCTCTTGGGCAACGGC |
| 52 | 766–795 | SEQ ID NO: 27 TCCGGCTCAGGGGCAGCGCCACGCCTGGGC |

TABLE I-continued hTRT AS 30-mers:

| PS-ODN# | Position *(3'–5') | 5'-AS sequence-3' SEQ ID NO; |
|---|---|---|
| 53 | 781–810 | SEQ ID NO: 28 CCAACGGGCGTCCGCTCCGGCTCAGGGGCA |
| 54 | 796–825 | SEQ ID NO: 29 GCCCAGGACCCCTGCCCAACGGGCGTCCGC |
| 62 | 916–945 | SEQ ID NO: 30 GGGTGGGAGTGGCGCGTGCCAGAGAGCGCA |
| 68 | 1006–1035 | SEQ ID NO: 31 TCGGCGTACACCGGGGACAAGGCGTGTCC |
| 69 | 1021–1050 | SEQ ID NO: 32 AGGAAGTGCTTGGTCTCGGCGTACACCGGG |
| 70 | 1036–1065 | SEQ ID NO: 33 TCGCCTGAGGAGTAGAGGAAGTGCTTGGTC |
| 71 | 1051–1080 | SEQ ID NO: 34 CGCAGCTGCTCCTTGTCGCCTGAGGAGTAG |
| 72 | 1066–1095 | SEQ ID NO: 35 AGTAGGAAGGAGGGCCGCAGCTGCTCCTTG |
| 73 | 1081–1110 | SEQ ID NO: 36 GGCCTCAGAGAGCTGAGTAGGAAGGAGGGC |
| 74 | 1096–1125 | SEQ ID NO: 37 GCGCCAGTCAGGCTGGGCCTCAGAGAGCTG |
| 75 | 1111–1140 | SEQ ID NO: 38 TCCACGAGCCTCCGAGCGCCAGTCAGGCTG |
| 76 | 1126–1155 | SEQ ID NO: 39 CCCAGAAAGATGGTCTCCACGAGCCTCCGA |
| 77 | 1141–1170 | SEQ ID NO: 40 ATCCAGGGCCTGGAACCCAGAAAGATGGTC |
| 80 | 1186–1215 | SEQ ID NO: 41 CAGTAGCGCTGGGGCAGGCGGGGCAACCTG |
| 81 | 1201–1230 | SEQ ID NO: 42 AGGGGCCGCATTTGCCAGTAGCGCTGGGGC |
| 82 | 1216–1245 | SEQ ID NO: 43 AGCAGCTCCAGAAACAGGGGCCGCATTTGC |
| 83 | 1231–1260 | SEQ ID NO: 44 TGCGCGTGGTTCCCAAGCAGCTCCAGAAAC |
| 84 | 1246–1275 | SEQ ID NO: 45 ACCCGTAGGGGCACTGCGCGTGGTTCCCA |
| 85 | 1261–1290 | SEQ ID NO: 46 TGCGTCTTGAGGAGCACCCCGTAGGGGCAC |
| 86 | 1276–1305 | SEQ ID NO: 47 GCTCGCAGCGGGCAGTGCGTCTTGAGGAGC |
| 87 | 1291–1320 | SEQ ID NO: 48 GCTGGGGTGACCGCAGCTCGCAGCGGGCAG |
| 88 | 1306–1335 | SEQ ID NO: 49 GCACAGACACCGGCTGCTGGGGTGACCGCA |
| 93 | 1381–1410 | SEQ ID NO: 50 AGCAGCTGCACCAGGCGACGGGGGTCTGTG |
| 94 | 1396–1425 | SEQ ID NO: 51 CTGCTGTGCTGGCGGAGCAGCTGCACCAGG |
| 96 | 1426–1455 | SEQ ID NO: 52 GCCCGCACGAAGCCGTACACCTGCCAGGGG |
| 100 | 1486–1515 | SEQ ID NO: 53 AAGCGGCGTTCGTTGTGCCTGGAGCCCCAG |
| 112 | 1666–1695 | SEQ ID NO: 54 CAGTGCAGGAACTTGGCCAGGATCTCCTCA |
| 114 | 1696–1725 | SEQ ID NO: 55 AGCAGCTCGACGACGTACACACTCATCAGC |
| 130 | 1936–1965 | SEQ ID NO: 56 TCCATGTTCACAATCGGCCGCAGCCCGTCA |
| 143 | 2131–2160 | SEQ ID NO: 57 GGGTCCTGGGCCCGCACACGCAGCACGAAG |
| 144 | 2146–2175 | SEQ ID NO: 58 TACAGCTCAGGCGGCGGGTCCTGGGCCCGC |
| 151 | 2251–2280 | SEQ ID NO: 59 CGCACGCAGTACGTGTCTGGGGTTTGATG |
| 152 | 2266–2295 | SEQ ID NO: 60 ACCACGGCATACCGACGCACGCAGTACGTG |
| 201 | 3001–3030 | SEQ ID NO: 61 TTCACCTGCAAATCCAGAAACAGGCTGTGA |
| 202 | 3016–3045 | SEQ ID NO: 62 ACCGTCTGGAGGCTGTTCACCTGCAAATCC |
| 203 | 3031–3060 | SEQ ID NO: 63 TAGATGTTGGTGCACACCGTCTGGAGGCTG |
| 208 | 3106–3135 | SEQ ID NO: 64 TTCCAAACTTGCTGATGAAATGGGAGCTGC |

TABLE I-continued hTRT AS 30-mers:

| PS-ODN# | Position *(3'–5') | 5'-AS sequence-3' SEQ ID NO; |
|---|---|---|
| 209 | 3121–3150 | SEQ ID NO: 65 AAAAATGTGGGGTTCTTCCAAACTTGCTGA |
| 210 | 3136–3165 | SEQ ID NO: 66 GAGATGACGCGCAGAAAAATGTGGGGTTC |
| 211 | 3151–3180 | SEQ ID NO: 67 AGGGAGGCCGTGTCAGAGATGACGCGCAGG |
| 212 | 3166–3195 | SEQ ID NO: 68 AGGATGGAGTAGCAGAGGGAGGCCGTGTCA |
| 213 | 3181–3210 | SEQ ID NO: 69 GCGTTCTTGGCTTTCAGGATGGAGTAGCAG |
| 230 | 3436–3465 | SEQ ID NO: 70 GCGGGTGGCCATCAGTCCAGGATGGTCTTG |
| 237 | 3541–3570 | SEQ ID NO: 71 CAGACTCCCAGCGGTGCGGGCCTGGGTGTG |
| 241 | 3601–3630 | SEQ ID NO: 72 AGCCGGACACTCAGCCTTCAGCCGGACATG |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters that could be changed or modified to yield essentially similar results.

Example I
Inhibition of hTRT Expression in vitro

In this example, inhibition of hTRT expression was examined using an in vitro cell-free expression system. A series of 30-mer antisense phosphorothioate oligonucleotides (PS-ODNs), which span the entire hTRT sequence, was systematically assayed for the ability to block hTRT expression in vitro (see FIG. 3). Co-expression of luciferase was used to normalize the samples and demonstrate the specificity of inhibition.

For inhibition of hTRT expression in vitro, an hTRT transcription/expression plasmid was prepared according to standard methodology for in vitro transcription and translation of hTRT RNA. Coupled transcription-translation reactions were performed with a reticulocyte lysate system (Promega TNT™) according to standard conditions (as performed in Example 7, U.S. patent application Ser. No. 08/974,549). Each coupled transcription/translation reaction included hTRT RNA transcribed from the expression plasmid, and a test antisense polynucleotide at a range of standard test concentrations, as well as the luciferase transcription/translation internal control (see, e.g., Sambrook et al., supra, Ausubel et al., supra). The translation reaction can also be performed with hTRT RNA that is synthesized in vitro in a separate reaction and then added to the translation reaction. $^{35}$S-Met was included in the reaction to label the translation products. The negative control was performed without added PS-ODN.

The labeled translation products were separated by gel electrophoresis and quantitated after exposing the gel to a phosphorimager screen. The amount of hTRT protein expressed in the presence of hTRT specific PS-ODNs was normalized to the co-expressed luciferase control. The data are presented in FIG. 3 as a percentage of the control, which is without added PS-ODN.

Example II
Inhibition of hTRT Expression Ex Vivo

A. Reagents

Cells: ACHN cells, NCI, catalogue #503755; 293 cells, ATCC; BJ (see, e.g., Kim et al., Science 266: 2011–2015 (1994)); additional cells from the ATCC or NCI.

Media and solutions: RPMI 1640 medium, BioWhitaker; DMEM/M199 medium, BioWhitaker; EMEM, BioWhitaker; Fetal Bovine Serum, Summit (stored frozen at −20° C., stored thawed at 4° C.); Trypsin-EDTA, GIBCO (catalogue #25300–054) (stored frozen at −20° C., stored thawed 4° C.; Isoton II (stored at RT); DMSO (stored at RT); oligonucleotides (see Table 1 and FIG. 3, stored in solution at −20° C.); PBS (Ca$^{++}$/Mg$^{++}$ free); TE; 10 mM Tris-HCL, pH 8.0; 1 mM EDTA.

To prepare oligonucleotide stocks: Dissolve oligonucleotide nucleotides (PS-ODNs) in the appropriate amount of TE to make a concentrated stock solution (1–20 mM).

B. Treatment of Cells Ex Vivo with Antisense hTRT Oligonucleotides

1. For plating cells prior to oligonucleotide treatment, stock cultures of cells in log-phase growth (in T75 flask) were used. ACNH, 293, and BJ cells were used in this assay. The media was removed by aspiration, and the cells were rinsed with 2–5 ml of PBS. 1 ml of trypsin-EDTA was added to the cells, swirled to distribute, and incubated for 2 minutes. The trypsin was inactivated with 9 ml of media. The cells were gently triturated with media. 200 µL of the cells were then counted with a Coulter counter and diluted to the appropriate volume and number of cells per well.

2. For 6-well dishes, 1.1×10$^5$ cells total per well, 2 ml/well were added. The cells were allowed to settle 4–6 h prior to any treatment with oligonucleotides. The amount of cells can be scaled up or down proportionally for 12-well, 100 mm, or 150 mm dishes. For example, for 12-well dishes, use $4.6 \times 10^4$ cells in 2 ml media; for 100 mm dishes use $6 \times 10^5$ cells in 10 ml media; for 150 mm dishes use $1.7 \times 10^6$ cells in 35 ml media.

3. Oligonucleotides were diluted in media and fed to the cells at a range of standard test concentrations. Serial, sterile dilutions of the ODNs (see, e.g., Table 1) were prepared in sterile, filtered media for feeding the cells. The cells were treated in single, duplicate, or triplicate wells. Control wells were treated with TE diluted in media.

4. The cells were fed daily with freshly diluted PS-ODN-media by aspirating the media and then feeding with 2 ml of freshly diluted oligonucleotide in media.

5. When cells were near 70–80% confluent (3–4 days), the number of cells was determined per well. The media was removed by aspiration, and the cells were rinsed twice with 2 ml PBS. 0.5 ml trypsin-EDTA was added to the cells, swirled, and incubated for 2 minutes. The cells were triturated gently with 2 ml media per well. 200 μL of cells were counted in a Coulter counter. If necessary, the cells are replated at $1.1 \times 10^5$ cells per well, 2 ml media per well, and fed with PS-ODN as described above.

6. Samples of the cells were also harvested for analysis of telomerase activity by TRAP activity. The cells can also be analyzed by isolating RNA and performing RT-PCR, by TRF measurement, or by telomere length measurement (see, e.g., Example section, U.S. patent application Ser. No. 08/974,549 for assay protocols).

7. The cell population doublings (PDLs) were calculated for each timepoint according to the following formula. PDLs (P): Pn=Pn-1+[((ln(Total # cells))−(ln(# cells plated))/ln(2)].

8. Graph PDL vs. time (in days) for the full dose range of each PS-ODN as compared to control untreated cells.

9. Steps 2–8 were repeated for the desired duration (usually 2–4 weeks) or until cell growth was inhibited significantly.

10. Table 1 shows exemplary oligonucleotides that were tested using this assay, and which inhibited telomerase expression and activity by approximately 50% or more.

What is claimed is:

1. An isolated antisense oligonucleotide that hybridizes to a target DNA having the nucleotide sequence of SEQ. ID NO:1 at 5° C. to 25° C. below $T_m$ in aqueous solution at 1 M NaCl;

wherein $T_m$ is the melting temperature of a complementary oligonucleotide hybridized to the target DNA in aqueous solution at 1 M NaCl, wherein the complementary oligonucleotide is exactly complementary to SEQ. ID NO:1 and the same length as the antisense oligonucleotide; and wherein hybridization of the antisense oligonucleotide to an mRNA encoding hTRT (SEQ. ID NO:1.)inhibits expression of the mRNA.

2. The oligonucleotide of claim 1 that hybridizes to the target DNA at 5° C. below $T_m$.

3. The oligonucleotide of claim 1 that is DNA.

4. The oligonucleotide of claim 1 that is RNA.

5. The oligonucleotide of claim 1 that comprises one or more synthetic nucleotides.

6. The oligonucleotide of claim 5 that comprises a phosphorothioate oligonucleotide.

7. The oligonucleotide of claim 1 that is from 20 to 100 nucleotides in length.

8. The oligonucleotide of claim 7 that is 30 nucleotides in length.

9. The oligonucleotide of claim 1 that is from 10 to 50 nucleotides in length.

10. The oligonucleotide of claim 1 that comprises a sequence of about 7 to about 100 nucleotides that is exactly complementary to SEQ. ID NO:1.

11. The oligonucleotide of claim 10 that is from 20 to 100 nucleotides in length.

12. The oligonucleotide of claim 11, wherein the oligonucleotide comprises a nucleotide sequence selected from the group consisting of SEQ ID NOS:4–72.

13. The oligonucleotide of claim 12, that is 30 nucleotides in length.

14. The oligonucleotide of claim 1, wherein said oligonucleotide reduces telomerase activity in a cell by at least 50%.

* * * * *

UNITED STATES PATENT AND TRADEMARK OFFICE
CERTIFICATE OF CORRECTION

| | | |
|---|---|---|
| PATENT NO. | : 6,444,650 B1 | Page 1 of 1 |
| APPLICATION NO. | : 09/052919 | |
| DATED | : September 3, 2002 | |
| INVENTOR(S) | : Cech et al. | |

It is certified that error appears in the above-identified patent and that said Letters Patent is hereby corrected as shown below:

Column 1,
Line 34, add -- This invention was made with Government support under Grant No. GM28039, awarded by the National Institutes of Health. The Government has certain rights in this invention. -- after "purposes".

Signed and Sealed this

Eleventh Day of July, 2006

JON W. DUDAS
*Director of the United States Patent and Trademark Office*

SEQUENCE LISTING (1) GENERAL INFORMATION:

(iii) NUMBER OF SEQUENCES: 72

(2) INFORMATION FOR SEQ ID NO:1:

(i) SEQUENCE CHARACTERISTICS:
      (A) LENGTH: 4015 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 56..3454
      (D) OTHER INFORMATION: /product= "human telomerase reverse
         transcriptase (hTRT)"

(xi) SEQUENCE DESCRIPTION: SEQ ID NO:1:

```
GCAGCGCTGC GTCCTGCTGC GCACGTGGGA AGCCCTGGCC CCGGCCACCC CCGCG ATG        58
                                                              Met
                                                               1

CCG CGC GCT CCC CGC TGC CGA GCC GTG CGC TCC CTG CTG CGC AGC CAC        106
Pro Arg Ala Pro Arg Cys Arg Ala Val Arg Ser Leu Leu Arg Ser His
          5                  10                  15

TAC CGC GAG GTG CTG CCG CTG GCC ACG TTC GTG CGG CGC CTG GGG CCC        154
Tyr Arg Glu Val Leu Pro Leu Ala Thr Phe Val Arg Arg Leu Gly Pro
         20                  25                  30

CAG GGC TGG CGG CTG GTG CAG CGC GGG GAC CCG GCG GCT TTC CGC GCG        202
Gln Gly Trp Arg Leu Val Gln Arg Gly Asp Pro Ala Ala Phe Arg Ala
     35                  40                  45

CTG GTG GCC CAG TGC CTG GTG TGC GTG CCC TGG GAC GCA CGG CCG CCC        250
Leu Val Ala Gln Cys Leu Val Cys Val Pro Trp Asp Ala Arg Pro Pro
 50                  55                  60                  65

CCC GCC GCC CCC TCC TTC CGC CAG GTG TCC TGC CTG AAG GAG CTG GTG        298
Pro Ala Ala Pro Ser Phe Arg Gln Val Ser Cys Leu Lys Glu Leu Val
                 70                  75                  80
```

-continued

```
GCC CGA GTG CTG CAG AGG CTG TGC GAG CGC GGC GCG AAG AAC GTG CTG        346
Ala Arg Val Leu Gln Arg Leu Cys Glu Arg Gly Ala Lys Asn Val Leu
            85                  90                  95

GCC TTC GGC TTC GCG CTG CTG GAC GGG GCC CGC GGG GGC CCC CCC GAG        394
Ala Phe Gly Phe Ala Leu Leu Asp Gly Ala Arg Gly Gly Pro Pro Glu
        100                 105                 110

GCC TTC ACC ACC AGC GTG CGC AGC TAC CTG CCC AAC ACG GTG ACC GAC        442
Ala Phe Thr Thr Ser Val Arg Ser Tyr Leu Pro Asn Thr Val Thr Asp
    115                 120                 125

GCA CTG CGG GGG AGC GGG GCG TGG GGG CTG CTG CTG CGC CGC GTG GGC        490
Ala Leu Arg Gly Ser Gly Ala Trp Gly Leu Leu Leu Arg Arg Val Gly
130                 135                 140                 145

GAC GAC GTG CTG GTT CAC CTG CTG GCA CGC TGC GCG CTC TTT GTG CTG        538
Asp Asp Val Leu Val His Leu Leu Ala Arg Cys Ala Leu Phe Val Leu
                150                 155                 160

GTG GCT CCC AGC TGC GCC TAC CAG GTG TGC GGG CCG CCG CTG TAC CAG        586
Val Ala Pro Ser Cys Ala Tyr Gln Val Cys Gly Pro Pro Leu Tyr Gln
            165                 170                 175

CTC GGC GCT GCC ACT CAG GCC CGG CCC CCG CCA CAC GCT AGT GGA CCC        634
Leu Gly Ala Ala Thr Gln Ala Arg Pro Pro Pro His Ala Ser Gly Pro
        180                 185                 190

CGA AGG CGT CTG GGA TGC GAA CGG GCC TGG AAC CAT AGC GTC AGG GAG        682
Arg Arg Arg Leu Gly Cys Glu Arg Ala Trp Asn His Ser Val Arg Glu
    195                 200                 205

GCC GGG GTC CCC CTG GGC CTG CCA GCC CCG GGT GCG AGG AGG CGC GGG        730
Ala Gly Val Pro Leu Gly Leu Pro Ala Pro Gly Ala Arg Arg Arg Gly
210                 215                 220                 225

GGC AGT GCC AGC CGA AGT CTG CCG TTG CCC AAG AGG CCC AGG CGT GGC        778
Gly Ser Ala Ser Arg Ser Leu Pro Leu Pro Lys Arg Pro Arg Arg Gly
                230                 235                 240

GCT GCC CCT GAG CCG GAG CGG ACG CCC GTT GGG CAG GGG TCC TGG GCC        826
Ala Ala Pro Glu Pro Glu Arg Thr Pro Val Gly Gln Gly Ser Trp Ala
            245                 250                 255

CAC CCG GGC AGG ACG CGT GGA CCG AGT GAC CGT GGT TTC TGT GTG GTG        874
His Pro Gly Arg Thr Arg Gly Pro Ser Asp Arg Gly Phe Cys Val Val
        260                 265                 270

TCA CCT GCC AGA CCC GCC GAA GAA GCC ACC TCT TTG GAG GGT GCG CTC        922
Ser Pro Ala Arg Pro Ala Glu Glu Ala Thr Ser Leu Glu Gly Ala Leu
    275                 280                 285

TCT GGC ACG CGC CAC TCC CAC CCA TCC GTG GGC CGC CAG CAC CAC GCG        970
Ser Gly Thr Arg His Ser His Pro Ser Val Gly Arg Gln His His Ala
290                 295                 300                 305

GGC CCC CCA TCC ACA TCG CGG CCA CCA CGT CCC TGG GAC ACG CCT TGT       1018
Gly Pro Pro Ser Thr Ser Arg Pro Pro Arg Pro Trp Asp Thr Pro Cys
                310                 315                 320

CCC CCG GTG TAC GCC GAG ACC AAG CAC TTC CTC TAC TCC TCA GGC GAC       1066
Pro Pro Val Tyr Ala Glu Thr Lys His Phe Leu Tyr Ser Ser Gly Asp
            325                 330                 335

AAG GAG CAG CTG CGG CCC TCC TTC CTA CTC AGC TCT CTG AGG CCC AGC       1114
Lys Glu Gln Leu Arg Pro Ser Phe Leu Leu Ser Ser Leu Arg Pro Ser
        340                 345                 350

CTG ACT GGC GCT CGG AGG CTC GTG GAG ACC ATC TTT CTG GGT TCC AGG       1162
Leu Thr Gly Ala Arg Arg Leu Val Glu Thr Ile Phe Leu Gly Ser Arg
    355                 360                 365

CCC TGG ATG CCA GGG ACT CCC CGC AGG TTG CCC CGC CTG CCC CAG CGC       1210
Pro Trp Met Pro Gly Thr Pro Arg Arg Leu Pro Arg Leu Pro Gln Arg
370                 375                 380                 385

TAC TGG CAA ATG CGG CCC CTG TTT CTG GAG CTG CTT GGG AAC CAC GCG       1258
Tyr Trp Gln Met Arg Pro Leu Phe Leu Glu Leu Leu Gly Asn His Ala
                390                 395                 400
```

```
CAG TGC CCC TAC GGG GTG CTC CTC AAG ACG CAC TGC CCG CTG CGA GCT      1306
Gln Cys Pro Tyr Gly Val Leu Leu Lys Thr His Cys Pro Leu Arg Ala
            405                 410                 415

GCG GTC ACC CCA GCA GCC GGT GTC TGT GCC CGG GAG AAG CCC CAG GGC      1354
Ala Val Thr Pro Ala Ala Gly Val Cys Ala Arg Glu Lys Pro Gln Gly
            420                 425                 430

TCT GTG GCG GCC CCC GAG GAG GAG GAC ACA GAC CCC CGT CGC CTG GTG      1402
Ser Val Ala Ala Pro Glu Glu Glu Asp Thr Asp Pro Arg Arg Leu Val
435                 440                 445

CAG CTG CTC CGC CAG CAC AGC AGC CCC TGG CAG GTG TAC GGC TTC GTG      1450
Gln Leu Leu Arg Gln His Ser Ser Pro Trp Gln Val Tyr Gly Phe Val
450                 455                 460                 465

CGG GCC TGC CTG CGC CGG CTG GTG CCC CCA GGC CTC TGG GGC TCC AGG      1498
Arg Ala Cys Leu Arg Arg Leu Val Pro Pro Gly Leu Trp Gly Ser Arg
                470                 475                 480

CAC AAC GAA CGC CGC TTC CTC AGG AAC ACC AAG AAG TTC ATC TCC CTG      1546
His Asn Glu Arg Arg Phe Leu Arg Asn Thr Lys Lys Phe Ile Ser Leu
            485                 490                 495

GGG AAG CAT GCC AAG CTC TCG CTG CAG GAG CTG ACG TGG AAG ATG AGC      1594
Gly Lys His Ala Lys Leu Ser Leu Gln Glu Leu Thr Trp Lys Met Ser
        500                 505                 510

GTG CGG GAC TGC GCT TGG CTG CGC AGG AGC CCA GGG GTT GGC TGT GTT      1642
Val Arg Asp Cys Ala Trp Leu Arg Arg Ser Pro Gly Val Gly Cys Val
515                 520                 525

CCG GCC GCA GAG CAC CGT CTG CGT GAG GAG ATC CTG GCC AAG TTC CTG      1690
Pro Ala Ala Glu His Arg Leu Arg Glu Glu Ile Leu Ala Lys Phe Leu
530                 535                 540                 545

CAC TGG CTG ATG AGT GTG TAC GTC GTC GAG CTG CTC AGG TCT TTC TTT      1738
His Trp Leu Met Ser Val Tyr Val Val Glu Leu Leu Arg Ser Phe Phe
                550                 555                 560

TAT GTC ACG GAG ACC ACG TTT CAA AAG AAC AGG CTC TTT TTC TAC CGG      1786
Tyr Val Thr Glu Thr Thr Phe Gln Lys Asn Arg Leu Phe Phe Tyr Arg
            565                 570                 575

AAG AGT GTC TGG AGC AAG TTG CAA AGC ATT GGA ATC AGA CAG CAC TTG      1834
Lys Ser Val Trp Ser Lys Leu Gln Ser Ile Gly Ile Arg Gln His Leu
        580                 585                 590

AAG AGG GTG CAG CTG CGG GAG CTG TCG GAA GCA GAG GTC AGG CAG CAT      1882
Lys Arg Val Gln Leu Arg Glu Leu Ser Glu Ala Glu Val Arg Gln His
595                 600                 605

CGG GAA GCC AGG CCC GCC CTG CTG ACG TCC AGA CTC CGC TTC ATC CCC      1930
Arg Glu Ala Arg Pro Ala Leu Leu Thr Ser Arg Leu Arg Phe Ile Pro
610                 615                 620                 625

AAG CCT GAC GGG CTG CGG CCG ATT GTG AAC ATG GAC TAC GTC GTG GGA      1978
Lys Pro Asp Gly Leu Arg Pro Ile Val Asn Met Asp Tyr Val Val Gly
                630                 635                 640

GCC AGA ACG TTC CGC AGA GAA AAG AGG GCC GAG CGT CTC ACC TCG AGG      2026
Ala Arg Thr Phe Arg Arg Glu Lys Arg Ala Glu Arg Leu Thr Ser Arg
            645                 650                 655

GTG AAG GCA CTG TTC AGC GTG CTC AAC TAC GAG CGG GCG CGG CGC CCC      2074
Val Lys Ala Leu Phe Ser Val Leu Asn Tyr Glu Arg Ala Arg Arg Pro
        660                 665                 670

GGC CTC CTG GGC GCC TCT GTG CTG GGC CTG GAC GAT ATC CAC AGG GCC      2122
Gly Leu Leu Gly Ala Ser Val Leu Gly Leu Asp Asp Ile His Arg Ala
675                 680                 685

TGG CGC ACC TTC GTG CTG CGT GTG CGG GCC CAG GAC CCG CCG CCT GAG      2170
Trp Arg Thr Phe Val Leu Arg Val Arg Ala Gln Asp Pro Pro Pro Glu
690                 695                 700                 705

CTG TAC TTT GTC AAG GTG GAT GTG ACG GGC GCG TAC GAC ACC ATC CCC      2218
Leu Tyr Phe Val Lys Val Asp Val Thr Gly Ala Tyr Asp Thr Ile Pro
```

|  |  | 710 |  |  |  | 715 |  |  |  | 720 |  |  |  |  |
|---|---|---|---|---|---|---|---|---|---|---|---|---|---|---|
| CAG | GAC | AGG | CTC | ACG | GAG | GTC | ATC | GCC | AGC | ATC | ATC | AAA | CCC | CAG AAC | 2266 |
| Gln | Asp | Arg | Leu | Thr | Glu | Val | Ile | Ala | Ser | Ile | Ile | Lys | Pro | Gln Asn |
|  |  | 725 |  |  |  | 730 |  |  |  | 735 |  |  |  |  |

| ACG | TAC | TGC | GTG | CGT | CGG | TAT | GCC | GTG | GTC | CAG | AAG | GCC | GCC | CAT GGG | 2314 |
| Thr | Tyr | Cys | Val | Arg | Arg | Tyr | Ala | Val | Val | Gln | Lys | Ala | Ala | His Gly |
|  |  | 740 |  |  |  | 745 |  |  |  | 750 |  |  |  |  |

| CAC | GTC | CGC | AAG | GCC | TTC | AAG | AGC | CAC | GTC | TCT | ACC | TTG | ACA | GAC CTC | 2362 |
| His | Val | Arg | Lys | Ala | Phe | Lys | Ser | His | Val | Ser | Thr | Leu | Thr | Asp Leu |
|  |  | 755 |  |  |  | 760 |  |  |  | 765 |  |  |  |  |

| CAG | CCG | TAC | ATG | CGA | CAG | TTC | GTG | GCT | CAC | CTG | CAG | GAG | ACC | AGC CCG | 2410 |
| Gln | Pro | Tyr | Met | Arg | Gln | Phe | Val | Ala | His | Leu | Gln | Glu | Thr | Ser Pro |
| 770 |  |  |  | 775 |  |  |  | 780 |  |  |  | 785 |  |  |

| CTG | AGG | GAT | GCC | GTC | GTC | ATC | GAG | CAG | AGC | TCC | TCC | CTG | AAT | GAG GCC | 2458 |
| Leu | Arg | Asp | Ala | Val | Val | Ile | Glu | Gln | Ser | Ser | Ser | Leu | Asn | Glu Ala |
|  |  |  | 790 |  |  |  | 795 |  |  |  | 800 |  |  |  |

| AGC | AGT | GGC | CTC | TTC | GAC | GTC | TTC | CTA | CGC | TTC | ATG | TGC | CAC | CAC GCC | 2506 |
| Ser | Ser | Gly | Leu | Phe | Asp | Val | Phe | Leu | Arg | Phe | Met | Cys | His | His Ala |
|  |  |  | 805 |  |  |  | 810 |  |  |  | 815 |  |  |  |

| GTG | CGC | ATC | AGG | GGC | AAG | TCC | TAC | GTC | CAG | TGC | CAG | GGG | ATC | CCG CAG | 2554 |
| Val | Arg | Ile | Arg | Gly | Lys | Ser | Tyr | Val | Gln | Cys | Gln | Gly | Ile | Pro Gln |
|  |  | 820 |  |  |  | 825 |  |  |  | 830 |  |  |  |  |

| GGC | TCC | ATC | CTC | TCC | ACG | CTG | CTC | TGC | AGC | CTG | TGC | TAC | GGC | GAC ATG | 2602 |
| Gly | Ser | Ile | Leu | Ser | Thr | Leu | Leu | Cys | Ser | Leu | Cys | Tyr | Gly | Asp Met |
| 835 |  |  |  | 840 |  |  |  | 845 |  |  |  |  |  |  |

| GAG | AAC | AAG | CTG | TTT | GCG | GGG | ATT | CGG | CGG | GAC | GGG | CTG | CTC | CTG CGT | 2650 |
| Glu | Asn | Lys | Leu | Phe | Ala | Gly | Ile | Arg | Arg | Asp | Gly | Leu | Leu | Leu Arg |
| 850 |  |  |  | 855 |  |  |  | 860 |  |  |  | 865 |  |  |

| TTG | GTG | GAT | GAT | TTC | TTG | TTG | GTG | ACA | CCT | CAC | CTC | ACC | CAC | GCG AAA | 2698 |
| Leu | Val | Asp | Asp | Phe | Leu | Leu | Val | Thr | Pro | His | Leu | Thr | His | Ala Lys |
|  |  |  | 870 |  |  |  | 875 |  |  |  | 880 |  |  |  |

| ACC | TTC | CTC | AGG | ACC | CTG | GTC | CGA | GGT | GTC | CCT | GAG | TAT | GGC | TGC GTG | 2746 |
| Thr | Phe | Leu | Arg | Thr | Leu | Val | Arg | Gly | Val | Pro | Glu | Tyr | Gly | Cys Val |
|  |  |  | 885 |  |  |  | 890 |  |  |  | 895 |  |  |  |

| GTG | AAC | TTG | CGG | AAG | ACA | GTG | GTG | AAC | TTC | CCT | GTA | GAA | GAC | GAG GCC | 2794 |
| Val | Asn | Leu | Arg | Lys | Thr | Val | Val | Asn | Phe | Pro | Val | Glu | Asp | Glu Ala |
|  |  | 900 |  |  |  | 905 |  |  |  | 910 |  |  |  |  |

| CTG | GGT | GGC | ACG | GCT | TTT | GTT | CAG | ATG | CCG | GCC | CAC | GGC | CTA | TTC CCC | 2842 |
| Leu | Gly | Gly | Thr | Ala | Phe | Val | Gln | Met | Pro | Ala | His | Gly | Leu | Phe Pro |
|  | 915 |  |  |  | 920 |  |  |  | 925 |  |  |  |  |  |

| TGG | TGC | GGC | CTG | CTG | CTG | GAT | ACC | CGG | ACC | CTG | GAG | GTG | CAG | AGC GAC | 2890 |
| Trp | Cys | Gly | Leu | Leu | Leu | Asp | Thr | Arg | Thr | Leu | Glu | Val | Gln | Ser Asp |
| 930 |  |  |  | 935 |  |  |  | 940 |  |  |  | 945 |  |  |

| TAC | TCC | AGC | TAT | GCC | CGG | ACC | TCC | ATC | AGA | GCC | AGT | CTC | ACC | TTC AAC | 2938 |
| Tyr | Ser | Ser | Tyr | Ala | Arg | Thr | Ser | Ile | Arg | Ala | Ser | Leu | Thr | Phe Asn |
|  |  |  | 950 |  |  |  | 955 |  |  |  | 960 |  |  |  |

| CGC | GGC | TTC | AAG | GCT | GGG | AGG | AAC | ATG | CGT | CGC | AAA | CTC | TTT | GGG GTC | 2986 |
| Arg | Gly | Phe | Lys | Ala | Gly | Arg | Asn | Met | Arg | Arg | Lys | Leu | Phe | Gly Val |
|  |  | 965 |  |  |  | 970 |  |  |  | 975 |  |  |  |  |

| TTG | CGG | CTG | AAG | TGT | CAC | AGC | CTG | TTT | CTG | GAT | TTG | CAG | GTG | AAC AGC | 3034 |
| Leu | Arg | Leu | Lys | Cys | His | Ser | Leu | Phe | Leu | Asp | Leu | Gln | Val | Asn Ser |
|  |  | 980 |  |  |  | 985 |  |  |  | 990 |  |  |  |  |

| CTC | CAG | ACG | GTG | TGC | ACC | AAC | ATC | TAC | AAG | ATC | CTC | CTG | CTG | CAG GCG | 3082 |
| Leu | Gln | Thr | Val | Cys | Thr | Asn | Ile | Tyr | Lys | Ile | Leu | Leu | Leu | Gln Ala |
|  | 995 |  |  |  | 1000 |  |  |  | 1005 |  |  |  |  |  |

| TAC | AGG | TTT | CAC | GCA | TGT | GTG | CTG | CAG | CTC | CCA | TTT | CAT | CAG | CAA GTT | 3130 |
| Tyr | Arg | Phe | His | Ala | Cys | Val | Leu | Gln | Leu | Pro | Phe | His | Gln | Gln Val |
| 1010 |  |  |  | 1015 |  |  |  | 1020 |  |  |  | 1025 |  |  |

| TGG | AAG | AAC | CCC | ACA | TTT | TTC | CTG | CGC | GTC | ATC | TCT | GAC | ACG | GCC TCC | 3178 |

-continued

```
Trp Lys Asn Pro Thr Phe Phe Leu Arg Val Ile Ser Asp Thr Ala Ser
              1030                1035                1040

CTC TGC TAC TCC ATC CTG AAA GCC AAG AAC GCA GGG ATG TCG CTG GGG       3226
Leu Cys Tyr Ser Ile Leu Lys Ala Lys Asn Ala Gly Met Ser Leu Gly
              1045                1050                1055

GCC AAG GGC GCC GCC GGC CCT CTG CCC TCC GAG GCC GTG CAG TGG CTG       3274
Ala Lys Gly Ala Ala Gly Pro Leu Pro Ser Glu Ala Val Gln Trp Leu
              1060                1065                1070

TGC CAC CAA GCA TTC CTG CTC AAG CTG ACT CGA CAC CGT GTC ACC TAC       3322
Cys His Gln Ala Phe Leu Leu Lys Leu Thr Arg His Arg Val Thr Tyr
              1075                1080                1085

GTG CCA CTC CTG GGG TCA CTC AGG ACA GCC CAG ACG CAG CTG AGT CGG       3370
Val Pro Leu Leu Gly Ser Leu Arg Thr Ala Gln Thr Gln Leu Ser Arg
1090              1095                1100                1105

AAG CTC CCG GGG ACG ACG CTG ACT GCC CTG GAG GCC GCA GCC AAC CCG       3418
Lys Leu Pro Gly Thr Thr Leu Thr Ala Leu Glu Ala Ala Ala Asn Pro
              1110                1115                1120

GCA CTG CCC TCA GAC TTC AAG ACC ATC CTG GAC TGATGGCCAC CCGCCCACAG     3471
Ala Leu Pro Ser Asp Phe Lys Thr Ile Leu Asp
              1125                1130

CCAGGCCGAG AGCAGACACC AGCAGCCCTG TCACGCCGGG CTCTACGTCC CAGGGAGGGA     3531

GGGGCGGCCC ACACCCAGGC CCGCACCGCT GGGAGTCTGA GGCCTGAGTG AGTGTTTGGC     3591

CGAGGCCTGC ATGTCCGGCT GAAGGCTGAG TGTCCGGCTG AGGCCTGAGC GAGTGTCCAG     3651

CCAAGGGCTG AGTGTCCAGC ACACCTGCCG TCTTCACTTC CCCACAGGCT GGCGCTCGGC     3711

TCCACCCCAG GGCCAGCTTT TCCTCACCAG GAGCCCGGCT TCCACTCCCC ACATAGGAAT     3771

AGTCCATCCC CAGATTCGCC ATTGTTCACC CCTCGCCCTG CCCTCCTTTG CCTTCCACCC     3831

CCACCATCCA GGTGGAGACC CTGAGAAGGA CCCTGGGAGC TCTGGGAATT TGGAGTGACC     3891

AAAGGTGTGC CCTGTACACA GGCGAGGACC CTGCACCTGG ATGGGGGTCC CTGTGGGTCA     3951

AATTGGGGGG AGGTGCTGTG GGAGTAAAAT ACTGAATATA TGAGTTTTTC AGTTTTGAAA     4011

AAAA                                                                  4015
```

(2) INFORMATION FOR SEQ ID NO:2:

(i) SEQUENCE CHARACTERISTICS:
  (A) LENGTH: 1132 amino acids
  (B) TYPE: amino acid
  (D) TOPOLOGY: linear (ii) MOLECULE TYPE: protein (xi) SEQUENCE DESCRIPTION: SEQ ID NO:2:

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110
```

-continued

```
Glu Ala Phe Thr Thr Ser Val Arg Ser Tyr Leu Pro Asn Thr Val Thr
        115                 120                 125
Asp Ala Leu Arg Gly Ser Gly Ala Trp Gly Leu Leu Arg Arg Val
        130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
            180                 185                 190
Pro Arg Arg Arg Leu Gly Cys Glu Arg Ala Trp Asn His Ser Val Arg
            195                 200                 205
Glu Ala Gly Val Pro Leu Gly Leu Pro Ala Pro Gly Ala Arg Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
            260                 265                 270
Val Ser Pro Ala Arg Pro Ala Glu Glu Ala Thr Ser Leu Glu Gly Ala
            275                 280                 285
Leu Ser Gly Thr Arg His Ser His Pro Ser Val Gly Arg Gln His His
        290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
        355                 360                 365
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Glu Asp Thr Asp Pro Arg Arg Leu
        435                 440                 445
Val Gln Leu Leu Arg Gln His Ser Ser Pro Trp Gln Val Tyr Gly Phe
    450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
        515                 520                 525
```

```
Val Pro Ala Ala Glu His Arg Leu Arg Glu Ile Leu Ala Lys Phe
    530                 535                 540
Leu His Trp Leu Met Ser Val Tyr Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
    850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
    930                 935                 940
Asp Tyr Ser Ser Tyr Ala Arg Thr Ser Ile Arg Ala Ser Leu Thr Phe
```

```
945                 950                 955                 960
Asn Arg Gly Phe Lys Ala Gly Arg Asn Met Arg Lys Leu Phe Gly
                965                 970                 975
Val Leu Arg Leu Lys Cys His Ser Leu Phe Leu Asp Leu Gln Val Asn
                980                 985                 990
Ser Leu Gln Thr Val Cys Thr Asn Ile Tyr Lys Ile Leu Leu Leu Gln
                995                1000                1005
Ala Tyr Arg Phe His Ala Cys Val Leu Gln Leu Pro Phe His Gln Gln
               1010                1015                1020
Val Trp Lys Asn Pro Thr Phe Phe Leu Arg Val Ile Ser Asp Thr Ala
1025               1030                1035                1040
Ser Leu Cys Tyr Ser Ile Leu Lys Ala Lys Asn Ala Gly Met Ser Leu
                1045                1050                1055
Gly Ala Lys Gly Ala Ala Gly Pro Leu Pro Ser Glu Ala Val Gln Trp
                1060                1065                1070
Leu Cys His Gln Ala Phe Leu Leu Lys Leu Thr Arg His Arg Val Thr
                1075                1080                1085
Tyr Val Pro Leu Leu Gly Ser Leu Arg Thr Ala Gln Thr Gln Leu Ser
                1090                1095                1100
Arg Lys Leu Pro Gly Thr Thr Leu Thr Ala Leu Glu Ala Ala Ala Asn
1105               1110                1115                1120
Pro Ala Leu Pro Ser Asp Phe Lys Thr Ile Leu Asp
                1125                1130

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:3:

TCCCACGTGC GCAGCAGGAC GCAGCGCTGC                                       30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:4:

GGCATCGCGG GGGTGGCCGG GGCCAGGGCT                                       30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"
```

(xi) SEQUENCE DESCRIPTION: SEQ ID NO:5:

CAGCGGGGAG CGCGCGGCAT CGCGGGGGTG                           30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:6:

AGCACCTCGC GGTAGTGGCT GCGCAGCAGG                           30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:7:

AACGTGGCCA GCGGCAGCAC CTCGCGGTAG                           30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:8:

GCGGGGGCG GCCGTGCGTC CCAGGGCACG                            30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:9:

CCGCGCTCGC ACAGCCTCTG CAGCACTCGG                           30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:10:

GGGGGGCCCC CGCGGGCCCC GTCCAGCAGC                               30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:11:

GTGGTGAAGG CCTCGGGGGG GCCCCCGCGG                               30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:12:

TAGCTGCGCA CGCTGGTGGT GAAGGCCTCG                               30

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:13:

ACCGTGTTGG GCAGGTAGCT GCGCACGCTG                               30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:14:

CGCAGTGCGT CGGTCACCGT GTTGGGCAGG                               30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "phosphorothioate oligonucleotide"

(xi) SEQUENCE DESCRIPTION: SEQ ID NO:15:

AGGTGAACCA GCACGTCGTC GCCCACGCGG                                           30

(2) INFORMATION FOR SEQ ID NO:16:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "phosphorothioate oligonucleotide"

(xi) SEQUENCE DESCRIPTION: SEQ ID NO:16:

GGGGGCCGGG CCTGAGTGGC AGCGCCGAGC                                           30

(2) INFORMATION FOR SEQ ID NO:17:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "phosphorothioate oligonucleotide"

(xi) SEQUENCE DESCRIPTION: SEQ ID NO:17:

CCACTAGCGT GTGGCGGGGG CCGGGCCTGA                                           30

(2) INFORMATION FOR SEQ ID NO:18:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "phosphorothioate oligonucleotide"

(xi) SEQUENCE DESCRIPTION: SEQ ID NO:18:

GCCCGTTCGC ATCCCAGACG CCTTCGGGGT                                           30

(2) INFORMATION FOR SEQ ID NO:19:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "phosphorothioate oligonucleotide"

(xi) SEQUENCE DESCRIPTION: SEQ ID NO:19:

ACGCTATGGT TCCAGGCCCG TTCGCATCCC                                           30

(2) INFORMATION FOR SEQ ID NO:20:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid
    (A) DESCRIPTION: /desc = "phosphorothioate oligonucleotide"

(xi) SEQUENCE DESCRIPTION: SEQ ID NO:20:

ACCCCGGCCT CCCTGACGCT ATGGTTCCAG                    30

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:21:

GGCAGGCCCA GGGGGACCCC GGCCTCCCTG                    30

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:22:

CTCGCACCCG GGGCTGGCAG GCCCAGGGGG                    30

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:23:

CTGCCCCCGC GCCTCCTCGC ACCCGGGGCT                    30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:24:

AGACTTCGGC TGGCACTGCC CCCGCGCCTC                    30

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:25:

CTCTTGGGCA ACGGCAGACT TCGGCTGGCA                                   30

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:26:

GCGCCACGCC TGGGCCTCTT GGGCAACGGC                                   30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:27:

TCCGGCTCAG GGGCAGCGCC ACGCCTGGGC                                   30

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:28:

CCAACGGGCG TCCGCTCCGG CTCAGGGGCA                                   30

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:29:

GCCCAGGACC CCTGCCCAAC GGGCGTCCGC                                   30

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:30:

GGGTGGGAGT GGCGCGTGCC AGAGAGCGCA                                30

(2) INFORMATION FOR SEQ ID NO:31:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:31:

TCGGCGTACA CCGGGGGACA AGGCGTGTCC                                30

(2) INFORMATION FOR SEQ ID NO:32:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:32:

AGGAAGTGCT TGGTCTCGGC GTACACCGGG                                30

(2) INFORMATION FOR SEQ ID NO:33:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:33:

TCGCCTGAGG AGTAGAGGAA GTGCTTGGTC                                30

(2) INFORMATION FOR SEQ ID NO:34:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:34:

CGCAGCTGCT CCTTGTCGCC TGAGGAGTAG                                30

(2) INFORMATION FOR SEQ ID NO:35:

(i) SEQUENCE CHARACTERISTICS:
            (A) LENGTH: 30 base pairs
            (B) TYPE: nucleic acid

```
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:35:

AGTAGGAAGG AGGGCCGCAG CTGCTCCTTG                                              30

(2) INFORMATION FOR SEQ ID NO:36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:36:

GGCCTCAGAG AGCTGAGTAG GAAGGAGGGC                                              30

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:37:

GCGCCAGTCA GGCTGGGCCT CAGAGAGCTG                                              30

(2) INFORMATION FOR SEQ ID NO:38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:38:

TCCACGAGCC TCCGAGCGCC AGTCAGGCTG                                              30

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:39:

CCCAGAAAGA TGGTCTCCAC GAGCCTCCGA                                              30

(2) INFORMATION FOR SEQ ID NO:40:

(i) SEQUENCE CHARACTERISTICS:
        (A) LENGTH: 30 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:40:

ATCCAGGGCC TGGAACCCAG AAAGATGGTC                                          30

(2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:41:

CAGTAGCGCT GGGGCAGGCG GGGCAACCTG                                          30

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:42:

AGGGGCCGCA TTTGCCAGTA GCGCTGGGGC                                          30

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:43:

AGCAGCTCCA GAAACAGGGG CCGCATTTGC                                          30

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:44:

TGCGCGTGGT TCCCAAGCAG CTCCAGAAAC                                          30

(2) INFORMATION FOR SEQ ID NO:45:

(i) SEQUENCE CHARACTERISTICS:

```
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:45:

ACCCCGTAGG GGCACTGCGC GTGGTTCCCA                                    30

(2) INFORMATION FOR SEQ ID NO:46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:46:

TGCGTCTTGA GGAGCACCCC GTAGGGGCAC                                    30

(2) INFORMATION FOR SEQ ID NO:47:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:47:

GCTCGCAGCG GGCAGTGCGT CTTGAGGAGC                                    30

(2) INFORMATION FOR SEQ ID NO:48:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:48:

GCTGGGGTGA CCGCAGCTCG CAGCGGGCAG                                    30

(2) INFORMATION FOR SEQ ID NO:49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:49:

GCACAGACAC CGGCTGCTGG GGTGACCGCA                                    30

(2) INFORMATION FOR SEQ ID NO:50:
```

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "phosphorothioate oligonucleotide"

(xi) SEQUENCE DESCRIPTION: SEQ ID NO:50:

AGCAGCTGCA CCAGGCGACG GGGGTCTGTG                                30

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:51:

CTGCTGTGCT GGCGGAGCAG CTGCACCAGG                                30

(2) INFORMATION FOR SEQ ID NO:52:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:52:

GCCCGCACGA AGCCGTACAC CTGCCAGGGG                                30

(2) INFORMATION FOR SEQ ID NO:53:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:53:

AAGCGGCGTT CGTTGTGCCT GGAGCCCCAG                                30

(2) INFORMATION FOR SEQ ID NO:54:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:54:

CAGTGCAGGA ACTTGGCCAG GATCTCCTCA                                30

(2) INFORMATION FOR SEQ ID NO:55:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:55:

AGCAGCTCGA CGACGTACAC ACTCATCAGC                                              30

(2) INFORMATION FOR SEQ ID NO:56:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:56:

TCCATGTTCA CAATCGGCCG CAGCCCGTCA                                              30

(2) INFORMATION FOR SEQ ID NO:57:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:57:

GGGTCCTGGG CCCGCACACG CAGCACGAAG                                              30

(2) INFORMATION FOR SEQ ID NO:58:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:58:

TACAGCTCAG GCGGCGGGTC CTGGGCCCGC                                              30

(2) INFORMATION FOR SEQ ID NO:59:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate oligonucleotide"

(xi) SEQUENCE DESCRIPTION: SEQ ID NO:59:

CGCACGCAGT ACGTGTTCTG GGGTTTGATG                                              30

(2) INFORMATION FOR SEQ ID NO:60:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:60:

ACCACGGCAT ACCGACGCAC GCAGTACGTG                                      30

(2) INFORMATION FOR SEQ ID NO:61:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:61:

TTCACCTGCA AATCCAGAAA CAGGCTGTGA                                      30

(2) INFORMATION FOR SEQ ID NO:62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:62:

ACCGTCTGGA GGCTGTTCAC CTGCAAATCC                                      30

(2) INFORMATION FOR SEQ ID NO:63:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:63:

TAGATGTTGG TGCACACCGT CTGGAGGCTG                                      30

(2) INFORMATION FOR SEQ ID NO:64:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:64:

TTCCAAACTT GCTGATGAAA TGGGAGCTGC                                      30

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:65:

AAAAATGTGG GGTTCTTCCA AACTTGCTGA                          30

(2) INFORMATION FOR SEQ ID NO:66:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:66:

GAGATGACGC GCAGGAAAAA TGTGGGGTTC                          30

(2) INFORMATION FOR SEQ ID NO:67:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:67:

AGGGAGGCCG TGTCAGAGAT GACGCGCAGG                          30

(2) INFORMATION FOR SEQ ID NO:68:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:68:

AGGATGGAGT AGCAGAGGGA GGCCGTGTCA                          30

(2) INFORMATION FOR SEQ ID NO:69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:69:

GCGTTCTTGG CTTTCAGGAT GGAGTAGCAG                          30

-continued (2) INFORMATION FOR SEQ ID NO:70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:70:

GCGGGTGGCC ATCAGTCCAG GATGGTCTTG       30

(2) INFORMATION FOR SEQ ID NO:71:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:71:

CAGACTCCCA GCGGTGCGGG CCTGGGTGTG       30

(2) INFORMATION FOR SEQ ID NO:72:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate oligonucleotide"

(xi) SEQUENCE DESCRIPTION: SEQ ID NO:72:

AGCCGGACAC TCAGCCTTCA GCCGGACATG       30